United States Patent
Gebeyehu et al.

(10) Patent No.: US 12,043,639 B2
(45) Date of Patent: Jul. 23, 2024

(54) POLYCATIONIC METHYL PHOSPHOLIPIDS FOR IMPROVED DELIVERY OF NUCLEIC ACIDS TO EUKARYOTIC CELLS

(71) Applicant: MOLECULAR TRANSFER, INC., Gaithersburg, MD (US)

(72) Inventors: Gulilat Gebeyehu, Potomac, MD (US); Joel Jessee, Mount Airy, MD (US)

(73) Assignee: Molecular Transfer, Inc., Gaitherbsurg, DE (US)

(*) Notice: Subject to any disclaimer, the term of this patent is extended or adjusted under 35 U.S.C. 154(b) by 603 days.

(21) Appl. No.: 17/222,442

(22) Filed: Apr. 5, 2021

(65) Prior Publication Data
US 2021/0323984 A1 Oct. 21, 2021

Related U.S. Application Data

(63) Continuation of application No. 16/222,740, filed on Dec. 17, 2018, now Pat. No. 10,968,240, which is a continuation of application No. 15/107,889, filed as application No. PCT/US2013/067157 on Oct. 28, 2013, now Pat. No. 10,155,780.

(60) Provisional application No. 61/719,932, filed on Oct. 29, 2012.

(51) Int. Cl.
| *C07F 9/10* | (2006.01) |
| *C07F 9/6506* | (2006.01) |
| *C12N 15/113* | (2010.01) |
| *C12N 15/88* | (2006.01) |
| *C12P 21/00* | (2006.01) |

(52) U.S. Cl.
CPC .......... *C07F 9/10* (2013.01); *C07F 9/106* (2013.01); *C07F 9/6506* (2013.01); *C12N 15/113* (2013.01); *C12N 15/88* (2013.01); *C12P 21/00* (2013.01); *C12N 2310/14* (2013.01)

(58) Field of Classification Search
None
See application file for complete search history.

(56) References Cited

U.S. PATENT DOCUMENTS

| 5,171,678 A | 12/1992 | Behr et al. |
| 6,172,049 B1 | 1/2001 | Dwyer et al. |
| 7,683,200 B2 | 3/2010 | Fang et al. |
| 10,155,780 B2 * | 12/2018 | Gebeyehu .......... C12N 15/88 |
| 10,968,240 B2 * | 4/2021 | Gebeyehu .......... C07F 9/106 |
| 2002/0052310 A1 | 5/2002 | Edwards et al. |
| 2003/0125517 A1 | 7/2003 | Cullis et al. |
| 2005/0026287 A1 | 2/2005 | Crouzet et al. |
| 2005/0260757 A1 | 11/2005 | Gebeyehu et al. |
| 2007/0014738 A1 | 1/2007 | Edwards et al. |
| 2012/0238747 A1 | 9/2012 | Chu et al. |

FOREIGN PATENT DOCUMENTS

| WO | 02053190 A2 | 7/2002 |
| WO | 2008075192 A2 | 6/2008 |
| WO | 2013028942 A2 | 2/2013 |

OTHER PUBLICATIONS

Malek and Khaledi (1999) "Expression and Analysis of Green Flourescent Proteins in Human Embryonic Kidney Cells by Capillary Electrophoresis" Analytical Biochemistry, 268: 262-69. (Year: 1999).*
Andresen, et al. (2004) "Enzymatic Release of Antitumor Ether Lipids by Specific Phospholipase A2 Activation of Liposome-Forming Prodrugs", Journal of Medicinal Chemistry, 47: 1694-1703.
Behr et al., Efficient gene transfer into mammalian primary endocrine cells with lipopolyamine-coated DNA. Proc Nall/Acad Sci US A. Sep. 1989;86{18):6982-6986.
Extended European Search Report issued in EP 13852277 dated Jun. 15, 2016—8 pages total.
International Preliminary Report on Patentability issued in PCT/US2013/067157 dated May 5, 2015—13 pages total.
International Search Report issued in PCT/US2013/067157 dated May 17, 2014—6 pages total.
Database CA [Online], "Preparation of tripeptide amide of phosphatidylethanolamine for liposomes", XP002758474, retrieved from STN Database accession No. 1992:531571 Jpn. Kokai Tokkyo Koho, 9 pp. Coden: JKXXAF, vol. JPH, No. 499795,Mar. 31, 1992 (1 page).
Felgner and Ringold, Cationic liposome-mediated transfection. Nature. Jan. 26, 1989;337(6205):387-388.
Felgner et al., Lipofection: a highly efficient, lipid-mediated DNA-transfection procedure. Proc Nall Acad Sci U S A. Nov. 1987;84(21):7413-7417.
Solodin et al., Synthesis Of Phosphotriester Cationic Phospholipids, Cationic Lipids 21. Synlell, May 1996; (5):457-458.

* cited by examiner

*Primary Examiner* — Robert M Kelly
(74) *Attorney, Agent, or Firm* — Vijay Gore

(57) ABSTRACT

New cationic lipids are provided that are useful for delivering macromolecules, such as nucleic acids, into eukaryotic cells. The lipids can be used alone, in combination with other lipids and/or in combination with other transfection enhancing reagents to prepare transfection complexes.

22 Claims, 9 Drawing Sheets
Specification includes a Sequence Listing.

POLYCATIONIC METHYL PHOSPHOLIPIDS FOR IMPROVED DELIVERY OF NUCLEIC ACIDS TO EUKARYOTIC CELLS

RELATED APPLICATIONS

The present invention is a continuation of U.S. patent application Ser. No. 16/222,740, filed Dec. 17, 2018, which is a continuation of U.S. patent application Ser. No. 15/107,889, filed Jun. 23, 2016, issued as U.S. Pat. No. 10,155,780, which is the U.S. national phase of International Application No. PCT/US2013/067157, filed Oct. 28, 2013, which designated the United States and claims priority from the U.S. Provisional Application Ser. No. 61/719,932, filed on Oct. 29, 2012, by Gebeyehu et al., and entitled "POLYCATIONIC METHYL PHOSPHOLIPIDS FOR IMPROVED DELIVERY OF NUCLEIC ACIDS TO EUKARYOTIC CELLS," the entire disclosure of each of which is incorporated by reference herein, including any drawings.

SEQUENCE LISTING

The instant application contains a Sequence Listing which has been submitted in ASCII format via EFS-Web and is hereby incorporated by reference in its entirety. Said ASCII copy, created on Dec. 17, 2018, is named LT01227CON_SeqListing.txt and is 9 kilobytes in size

FIELD OF THE INVENTION

The present invention is in the field of molecular biology, and more particularly in the field of transfection, which utilizes new compounds and methods for the introduction of nucleic acids into eukaryotic cells.

BACKGROUND OF THE DISCLOSURE

Transfection is the process of introducing nucleic acids into eukaryotic cells by non-viral methods. This gene transfer technology uses various physical or chemical methods to study gene function and protein expression in the context of a cell. Transfection applications have increased due to the development of reporter gene systems and selection methods for stable maintenance and expression of transferred DNA. The availability of transfection reagents together with assay-based reporter technology allows for the study of mammalian promoter and enhancer sequences, trans-acting proteins such as transcription factors, mRNA processing, protein-protein interactions, translation and recombinant events.

Transfection methods allow the introduction of negatively charged molecules (e.g. phosphate backbones of DNA and RNA) into cells having a negatively charged membrane. Physical methods like microinjection or electroporation simply punch through the membrane and introduce the DNA directly into the cytoplasm. Chemicals such as calcium phosphate and DEAE-dextran, or cationic lipid-based reagents coat the DNA, neutralizing or even creating an overall positive charge to the molecule. The DNA-transfection reagent complex easily crosses the cell membrane, especially for lipids that have a "fusogenic" component, which enhances fusion with the lipid bilayer of the cell.

There is a plethora of transfection reagents based on a cationic lipid that have been used to deliver large anionic molecules, such as nucleic acids, into certain types of cells (see Feigner et al., Nature 337:387-388 (1989); Proc. Natl. Acad Sci. USA 84:7413 (1987); Behr et al., Proc. Natl. Acad Sci. USA 86: 6982 (1989)). Both mono- and polycationic lipids have been used alone or in combination with other reagents, for delivery of these macromolecules. A large number of cationic lipids are commercially available. These agents are not, however, universally effective in all cell types and have the added drawback of being toxic. In many cases, the cationic lipids have to be used in combination with other reagents such as peptides to be effective in transfection. Moreover, these reagents require relatively complex protocols and are inconvenient to use.

It is apparent; therefore, that there is still a need for transfection reagents that are less toxic than the existing reagents and are universally effective. In particular, improved methods and transfection reagents are needed for introducing nucleic acids into primary cells as well as for the delivery of particular nucleic acids such as siRNA into cells.

SUMMARY OF THE INVENTION

Disclosed herein are new compounds, compositions and methods that improve the efficiency of introducing macromolecules, such as nucleic acids, into cells. New compounds are provided, together with compositions containing these compounds and methods for using these new compounds and compositions for transfection. The new compounds may be used alone for transfection, or they may be used in combination with additional reagents in transfection compositions. For example, the new compounds may be combined with one or more cationic lipids and/or neutral lipids, with one or more cell surface ligands, with one or more fusion enhancing agents, and with one or more nuclear localization agents and one or more amphipathic peptides and any combinations thereof. The resulting compositions may be complexed with one or more macromolecules or nucleic acids, such as DNA or RNA, and used to deliver these macromolecules into eukaryotic cells.

Thus, in one embodiment, the disclosure provides a compound having Formula I:

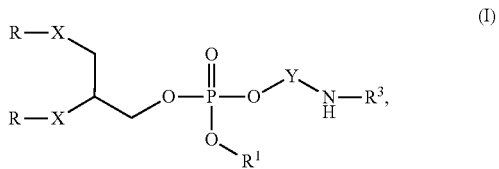

(I)

or a pharmaceutically acceptable salt thereof, wherein:
each X is independently selected from —O—, —OC(O)O—, —C(O)O—, —O(O)C—, —N($R^2$)C(O)O—, —C(O)N($R^2$)—, —OC(O)N($R^2$)—, and —($R^2$)NCON($R^2$)—;
Y is independently ($C_1$-$C_6$)alkyl;
each R is independently selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, and substituted or unsubstituted arylalkyl, wherein each R group is optionally independently substituted by 1-3 substituent groups, each substituent group independently selected from amino, hydroxyl, $(CH_2)_jOR^{11}$, $(CH_2)_jC(O)R^{11}$, $(CH_2)_jC(O)OR^{11}$, $(CH_2)_jOC(O)R^{11}$, $(CH_2)_jNR^{12}R^{13}$, $(CH_2)_jC(O)NR^{12}R^{13}$, $(CH_2)_jOC(O)NR^{12}R^{13}$, $(CH_2)_jN^{14}RC(O)R^{11}$, $(CH_2)_jN^{14}RC(O)OR^{11}$, $(CH_2)_jN^{14}RC(O)NR^{12}R^{13}$, and $(CH_2)_jN^{14}RC$ (NH)NR$^{12}$R$^{13}$, wherein each j is independently an integer selected from 0 to 6;

R$^1$ is independently selected from alkyl, (CH$_2$)$_j$OR$^{11}$, (CH$_2$)$_j$C(O)R$^{11}$, and CH$_2$CH(OH)CH$_2$(OH);

R$^2$ is independently selected from hydrogen and (C$_1$-C$_6$) alkyl;

R$^3$ is independently selected from hydrogen, —(CH$_2$)$_j$NR$^{12}$R$^{13}$, —C(O)CH[(CH$_2$)$_3$NH(CH$_2$)$_3$NH$_2$]—[NH(CH$_2$)$_3$NH$_2$], —C(O)CH(NH$_2$)(C H$_2$)$_3$NH$_2$; —C(O)CH(NH$_2$)(CH$_2$)$_4$NH$_2$, —C(O)CH(NH$_2$)(CH$_2$)$_3$NHC(=NH)NH$_2$, —C(O)CH(NH$_2$)(C H$_2$)(C$_3$H$_3$N$_2$), —C(O)CH(NH$_2$)(CH$_2$)$_3$NH$_2$, —C(O)CH(NH$_2$)CH$_2$NH$_2$, —C(O)CH(NH$_2$)(CH$_2$)$_2$NH$_2$, and —C(O)CH(NH$_2$)CHOH;

R$^{11}$, R$^{12}$, R$^{13}$ and R$^{14}$ are each independently selected from hydrogen, alkyl, alkenyl, alkynyl, perfluoroalkyl, and cycloalkyl, where the alkyl or alkenyl is optionally substituted with one or more substituent selected from the group consisting of amino, primary amino, secondary amino, hydroxy, alkoxy, and hydroxy alkyl.

In other embodiments, the disclosure provides compositions and methods for introducing a nucleic acid, protein, or peptide into a eukaryotic cell by contacting the cell with a compound of Formula I or a composition thereof, thereby introducing the nucleic acid, protein, or peptide into the cell.

DETAILED DESCRIPTION OF THE EMBODIMENTS

Definitions

Figure 1:
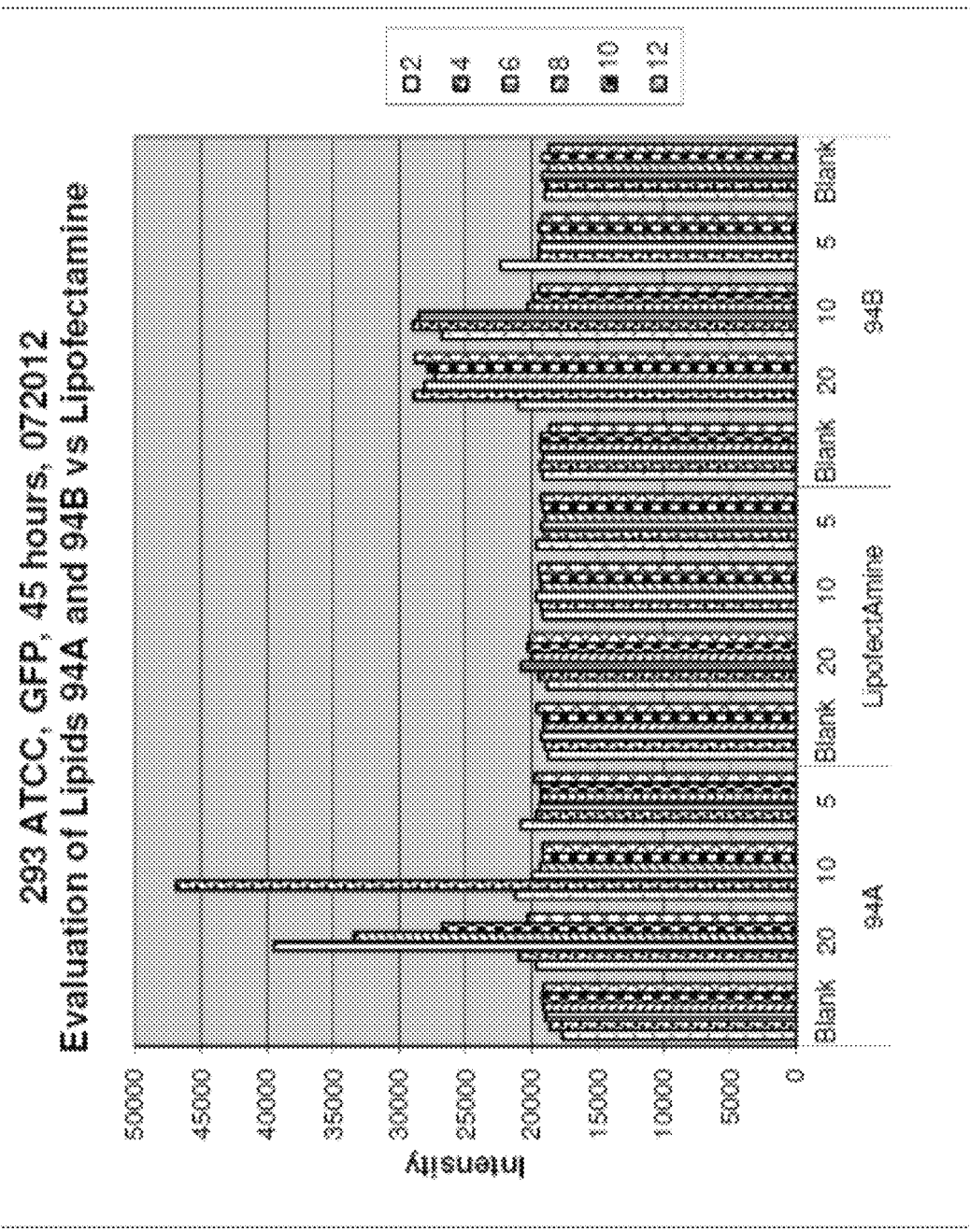
FIG. 1 shows the transfection evaluation of lipids 94-a and 94-b in 293 ATCC cells. The delivery and expression of the plasmid CMV•GFP in 293 ATCC cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time

The term "alkyl", alone or in combination with any other term, refers to a straight-chain or branch-chain saturated aliphatic hydrocarbon radical containing the specified number of carbon atoms, or where no number is specified, in one embodiment from 1 to about 20 (i.e. (C$_{1-20}$)alkyl), in another embodiment from 1 to about 10 carbon atoms (i.e. (C$_{1-10}$) alkyl), and in another embodiment from 1 to about 6 carbon atoms (i.e. (C$_{1-6}$)alkyl).

Examples of alkyl radicals include, but are not limited to, methyl, ethyl, n-propyl, isopropyl, n-butyl, isobutyl, sec-butyl, tert-butyl, pentyl, isoamyl, n-hexyl, lauryl, palmityl, stearyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, in one embodiment from 2-20 carbon atoms (i.e. (C$_{2-20}$)alkenyl) and in another embodiment, from 2-6 carbon atoms (i.e. (C$_{2-6}$)alkenyl). Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl, oleoyl, palmitoleoyl and the like.

The term "alkynyl," alone or in combination with any other term, refers to a straight-chain or branched-chain hydrocarbon radical having one or more triple bonds containing the specified number of carbon atoms, or where no number is specified, in one embodiment from 2 to about 20 carbon atoms. Examples of alkynyl radicals include, but are not limited to, ethynyl, propynyl, propargyl, butynyl, pentynyl and the like.

The term "alkoxy" refers to an alkyl, alkenyl or alkynyl ether radical, wherein the terms "alkyl", "alkenyl" or "alkynyl" are defined above. Examples of suitable alkyl ether radicals include, but are not limited to, methoxy, ethoxy, n-propoxy, isopropoxy, n-butoxy, isobutoxy, sec-butoxy, tert-butoxy, oleyloxy, palmityloxy, palmitoleoyloxy and the like.

The term "aryl," alone or in combination with any other term, refers to a carbocyclic aromatic radical (such as phenyl or naphthyl) containing the specified number of carbon atoms, in one embodiment from 6-15 carbon atoms (i.e. ($C_{6-15}$)aryl), and in another embodiment from 6-10 carbon atoms (i.e. ($C_{6-10}$)aryl), optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O-alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl (carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkyl alkyl radicals and the like.

The term "aminoalkanoyl" means an acyl radical derived from an amino substituted alkanecarboxylic acid wherein the amino group can be a primary, secondary or tertiary amino group containing substituents selected from hydrogen, cycloalkyl, cycloalkylalkyl radicals and the like, examples of which include N,N-dimethylaminoacetyl and N-benzylaminoacetyl.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Carbocycles in one embodiment have 5-7 carbons.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, in one embodiment from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "basic heterocycle" refers to a stable 5-7 membered monocyclic heterocyclic ring or 8-11 membered bicyclic heterocyclic ring which is either saturated or partially unsaturated, and which may be optionally benzofused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from nitrogen, oxygen and sulfur, provided that at least one heteroatom is a basic nitrogen atom. A heterocyclyl radical may be attached at any endocyclic carbon or heteroatom which results in the creation of a stable structure. Heterocycles include 5-7 membered monocyclic heterocycles and 8-10 membered bicyclic heterocycles. Examples of basic heterocycles include imidazolinoyl, imidazolidinyl, indazolinolyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, and oxoazepinyl.

The term "halogen" means fluorine, chlorine, bromine or iodine.

The term "surface ligand" or "cell surface ligand" refers to a chemical compound or structure which will bind to a surface receptor of a cell. The term "cell surface receptor" as used herein refers to a specific chemical grouping on the surface of a cell to which the ligand can attach. Cell surface receptors can be specific for a particular cell, i.e., found predominantly in one cell rather than in another type of cell (e.g., LDL and asialoglycoprotein receptors are specific for hepatocytes). The receptor facilitates the internalization of the ligand and attached molecules. A cell surface receptor includes but is not limited to a folate receptor, biotin receptor, lipoic acid receptor, low-density lipoprotein receptor, asialoglycoprotein receptor, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor, bone morphogenetic protein receptor, cartilage induction factor receptor or glycosylphosphatidylinositol (GPI)-anchored proteins (e.g., β-andrenargic receptor, T-cell activating protein, Thy-1 protein, GPI-anchored 5' nucleotidase). These are nonlimiting examples.

A receptor is a molecule to which a ligand binds specifically and with relatively high affinity. It is usually a protein or a glycoprotein, but may also be a glycolipid, a lipidpolysaccharide, a glycosaminoglycan or a glycocalyx. For purposes of this disclosure, epitopes to which an antibody or its fragments binds is construed as a receptor since the antigen: antibody complex undergoes endocytosis. Furthermore, surface ligand includes anything which is capable of entering the cell through cytosis (e.g. endocytosis, potocytosis, pinocytosis).

As used herein, the term "ligand" refers to a chemical compound or structure which will bind to a receptor. This includes but is not limited to ligands such as asialooroso-mucoid, asialoglycoprotein, lipoic acid, biotin, apolipoprotein E sequence, insulin-like growth factor II, calcitonin gene-related peptide, thymopoietin, hepatocyte growth factor, endothelin-1, atrial natriuretic factor, RGD-containing cell adhesion peptides and the like.

One skilled in the art will readily recognize that the ligand chosen will depend on which receptor is being bound. Since different types of cells have different receptors, this provides a method of targeting nucleic acid to specific cell types, depending on which cell surface ligand is used. Thus, the preferred cell surface ligand may depend on the targeted cell type.

The term "nuclear localization agent," "nuclear localization signal," or "nuclear ligand" as used herein refers to a ligand, such as a peptide, which will cause an agent covalently or non-covalently linked to it to localize at the cell nucleus, typically by binding a nuclear receptor. The term "nuclear receptor" as used herein refers to a chemical grouping on the nuclear membrane which will bind a specific ligand and help transport the ligand, and accompanying linked moieties, through the nuclear membrane. Nuclear receptors can be but are not limited to those receptors which bind nuclear localization sequences. Non-limiting examples of nuclear ligands include GYSTPPKKKRKVEDP (SEQ ID NOT), GYSTPPKTRRRP (SEQ ID NO:2), GYSTPGRKKR (SEQ ID NOT), GYSTPRRNRRRRW (SEQ ID NOT), PDEVKRKKKPPTSYG (SEQ ID NOT), PRRRTKPPT-SYG (SEQ ID NOT), RKKRGPTSYG (SEQ ID NO:7), WRRRRNRRPTSYG (SEQ ID NOT), and GYGPPKKKRKVEAPYKA(K)$_{8-40}$K (SEQ ID NO:9), may be used to transport nucleic acid to the nucleus.

The term "lysis agent" as used herein refers to a molecule, compound, protein or peptide which is capable of breaking down an endosomal membrane and freeing the DNA transporter into the cytoplasm of the cell. This term includes but is not limited to viruses, synthetic compounds, lytic peptides, or derivatives thereof. The term "lytic peptide" refers to a chemical grouping which penetrates a membrane such that the structural organization and integrity of the membrane is lost. As a result of the presence of the lysis agent, the membrane undergoes lysis, fusion or both.

The term "polycationic nucleic acid binding moiety" as used herein refers to a moiety containing multiple positive charges at physiological pH that allow the moiety to bind a negatively charged nucleic acid. A polycationic nucleic acid binding moiety may be linked to, for example, a cell surface ligand, a fusion agent, and/or a nuclear localization peptide. The linkage may be covalent. Suitable polycationic nucleic acid binding moieties include polyamines such as PEI, spermine, spermidine, carboxyspermine and polybasic peptides containing, for example, multiple lysine, ornithine, histidine, or arginine residues.

The term "nucleic acid," when not applied to a specific type of molecule such as unmodified DNA or RNA, refers to any type of nucleic acid that presently is known or that may be prepared or identified in the future, provided that the nucleic acid is sufficiently negatively charged to form a lipid aggregate, liposome, or liposome-like complex when admixed with any lipid of Formula I. Nucleic acid, as used herein, refers to deoxyribonucleotides or ribonucleotides and mixtures and polymers thereof in single- or double-stranded form. The term encompasses nucleic acids containing known nucleotide analogs or modified backbone residues or linkages, which are synthetic, naturally occurring, and non-naturally occurring, which have similar binding properties as a reference nucleic acid, and which are metabolized in a manner similar to a reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The nucleic acid may be in the form of an antisense molecule, for example a "gap-mer" containing an RNA-DNA-RNA structure that activates RNAseH. The nucleic acid can be, for example, DNA or RNA, or RNA-DNA hybrid, and can be an oligonucleotide, plasmid, parts of a plasmid DNA, pre-condensed DNA, product of a polymerase chain reaction (PCR), vectors, expression cassettes, chimeric sequences, chromosomal DNA, or derivatives of these groups or other form of nucleic acid molecule. The nucleic acid may be a double-stranded RNA molecule of the type used for inhibiting gene expression by RNA interference. The nucleic acid may be a short interfering double stranded RNA molecule (siRNA). The nucleic acid molecule can also be a Stealth™ RNAi molecule (Invitrogen Corporation/Life Technologies Corporation, Carlsbad, CA).

Compounds of Formula I

It has been found that compounds based on a core structure of Formula I are useful for the efficient delivery of macromolecules into eukaryotic cells. The compositions and methods are effective in a wide variety of cells, and provide a high efficiency of transfection. These compounds advantageously can be used with one or more neutral lipids and additional components such as fusogenic or fusion-enhancing molecules, additional cationic lipids, cell surface ligands, cell adhesion molecules, amphipathic peptides and nuclear localization agents, in a complex with the macromolecule. The complex is easily prepared by straightforward methods and can be used on a wide variety of cells.

In one embodiment, the disclosure provides a compound of Formula I:

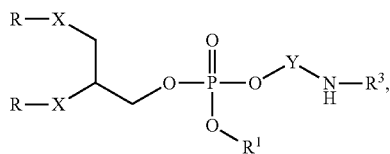

(I)

or a pharmaceutically acceptable salt thereof, wherein:
each X independently is selected from —O—, —OC(O)O—, —C(O)O—, —O(O)C—, —N($R^2$)C(O)O—, —C(O)N($R^2$)—, —OC(O)N($R^2$)—, and —($R^2$)NCON($R^2$)—;

Y is independently ($C_1$-$C_6$)alkyl;

each R is independently selected from substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, and substituted or unsubstituted arylalkyl, wherein each R group is optionally independently substituted by 1-3 substituent groups, each substituent group independently selected from amino, hydroxyl, $(CH_2)_jOR^{11}$, $(CH_2)_jC(O)R^{11}$, $(CH_2)_jC(O)OR^{11}$, $(CH_2)_jOC(O)R^{11}$, $(CH_2)_jNR^{12}R^{13}$, $(CH_2)_jC(O)NR^{12}R^{13}$, $(CH_2)_jOC(O)NR^{12}R^{13}$, $(CH_2)_jN^{14}RC(O)R^{11}$, $(CH_2)_jN^{14}RC(O)OR^{11}$, $(CH_2)_jN^{14}RC(O)NR^{12}R^{13}$, and $(CH_2)_jN^{14}RC(NH)NR^{12}R^{13}$, wherein each j is independently an integer selected from 0 to 6;

$R^1$ is independently selected from alkyl, $(CH_2)_jOR^{11}$, $(CH_2)_jC(O)R^{11}$, and $CH_2CH(OH)CH_2(OH)$;

$R^2$ is independently selected from hydrogen and ($C_1$-$C_6$) alkyl;

$R^3$ is independently selected from H, $(CH_2)_jNR^{12}R^{13}$, $C(O)CH[(CH_2)_3NH(CH_2)_3NH_2]$—$[NH(CH_2)_3NH_2]$, $C(O)CH(NH_2)(CH_2)_3NH_2$; $C(O)CH(NH_2)(CH_2)_4NH_2$, $C(O)CH(NH_2)(CH_2)_3NHC(=NH)NH_2$, $C(O)CH(NH_2)(CH_2)(C_3H_3N_2)$, —$C(O)CH(NH_2)(CH_2)_3NH_2$, —$C(O)CH(NH_2)CH_2NH_2$, —$C(O)CH(NH_2)(CH_2)_2NH_2$, and —$C(O)CH(NH_2)CHOH$;

$R^{11}$, $R^{12}$, $R^{13}$ and $R^{14}$ are each independently selected from hydrogen, alkyl, alkenyl, alkynyl, perfluoroalkyl, and cycloalkyl, where the alkyl or alkenyl is optionally substituted with one or more substituent selected from the group consisting of amino, primary amino, secondary amino, hydroxy, alkoxy, and hydroxy alkyl.

In another aspect, the disclosure provides compounds of Formula I, wherein:
each X independently is selected from —O—, —C(O)O—, —O(O)C—, —N($R^2$)C(O)O—, —C(O)N($R^2$)—, —OC(O)N($R^2$)—, —($R^2$)NCON($R^2$)—;

Y is independently ($C_1$-$C_4$)alkyl;

each R is independently selected from substituted or unsubstituted ($C_1$-$C_{20}$)alkyl, substituted or unsubstituted ($C_2$-$C_{20}$)alkenyl, and substituted or unsubstituted ($C_2$-$C_{20}$)alkynyl;

$R^1$ is independently selected from ($C_1$-$C_6$)alkyl, $C(O)R^{11}$, and $CH_2CH(OH)CH_2(OH)$;

$R^2$ is independently selected from hydrogen and ($C_1$-$C_4$) alkyl;

$R^3$ is independently selected from $(CH_2)_jNH_2$, $C(O)CH[(CH_2)_3NH(CH_2)_3NH_2]$—$[NH(CH_2)_3NH_2]$, $C(O)CH(NH_2)(CH_2)_3NH_2$; $C(O)CH(NH_2)(CH_2)_4NH_2$, $C(O)CH(NH_2)(CH_2)_3NHC(=NH)NH_2$, $C(O)CH(NH_2)(CH_2)(C_3H_3N_2)$, —$C(O)CH(NH_2)(CH_2)_3NH_2$, —$C(O)CH(NH_2)CH_2NH_2$, —$C(O)CH(NH_2)(CH_2)_2NH_2$, and —$C(O)CH(NH_2)CHOH$;

$R^{11}$ is independently selected from hydrogen, ($C_1$-$C_6$) alkyl, ($C_2$-$C_6$)alkenyl, ($C_2$-$C_6$)alkynyl, trifluoromethyl, and ($C_3$-$C_8$)cycloalkyl.

In another aspect, the disclosure provides compounds of Formula I, wherein:
each X independently is selected from —C(O)O—, —O(O)C—, and —C(O)N($R^2$)—;

Y is independently ($C_2$-$C_3$)alkyl;

each R is independently selected from ($C_1$-$C_{20}$)alkyl, ($C_2$-$C_{20}$)alkenyl, and ($C_2$-$C_{20}$)alkynyl;

$R^1$ is independently selected from ($C_1$-$C_6$)alkyl, $C(O)R^{11}$, and $CH_2CH(OH)CH_2(OH)$;

$R^2$ is independently selected from hydrogen and ($C_1$-$C_2$) alkyl; and $R^3$ is independently selected from $(CH_2)_jNH_2$, —$C(O)CH[(CH_2)_3NH(CH_2)_3NH_2]$—$[NH(CH_2)_3NH_2]$, —$C(O)CH(NH_2)(CH_2)_3NH_2$; —$C(O)CH(NH_2)(CH_2)_4NH_2$, —$C(O)CH(NH_2)(CH_2)_3NHC(=NH)NH_2$, —$C(O)CH(NH_2)(CH_2)(C_3H_3N_2)$, —$C(O)CH(NH_2)(CH_2)_3NH_2$, —$C(O)CH(NH_2)CH_2NH_2$, —$C(O)CH(NH_2)(CH_2)_2NH_2$, and —$C(O)CH(NH_2)CHOH$;

$R^{11}$ is independently selected from hydrogen and ($C_1$-$C_6$) alkyl.

In another aspect, the disclosure provides compounds of Formula I, wherein:
each X independently is selected from —C(O)O— and —O(O)C—;

Y is independently $CH_2CH_2$;

each R is independently selected from ($C_2$-$C_{20}$)alkyl and ($C_2$-$C_{20}$)alkenyl;

$R^1$ is independently selected from $CH_3$, $CH_2CH_3$, $CH_2CH_2CH_3$, $CH(CH_3)_2$, $CH_2CH_2CH_2CH_3$, $CH_2CH(CH_3)CH_3$, $C(CH_3)_3$, $C(O)CH_3$, $C(O)CH_2CH_3$, $C(O)CH_2CH_2CH_3$, $C(O)CH(CH_3)_2$, $C(O)CH_2CH_2CH_2CH_3$, $C(O)CH_2CH(CH_3)CH_3$, $C(O)C(CH_3)_3$, and $CH_2CH(OH)CH_2(OH)$;

$R^2$ is independently selected from hydrogen and $CH_3$, and $R^3$ is independently selected from —$(CH_2)_jNH_2$, —$C(O)CH[(CH_2)_3NH(CH_2)_3NH_2]$—$[NH(CH_2)_3NH_2]$, —$C(O)CH(NH_2)(CH_2)_3NH_2$; —$C(O)CH(NH_2)(CH_2)_4NH_2$, —$C(O)CH(NH_2)(CH_2)_3NHC(=NH)NH_2$, —$C(O)CH(NH_2)(CH_2)(C_3H_3N_2)$, —$C(O)CH(NH_2)(CH_2)_3NH_2$, —$C(O)CH(NH_2)CH_2NH_2$, —$C(O)CH(NH_2)(CH_2)_2NH_2$, and —$C(O)CH(NH_2)CHOH$; and $R^{11}$ is independently selected from hydrogen and $CH_3$.

In another aspect, the disclosure provides compounds of Formula I, wherein the compound of Formula I is selected from the compounds I-1 through I-14:

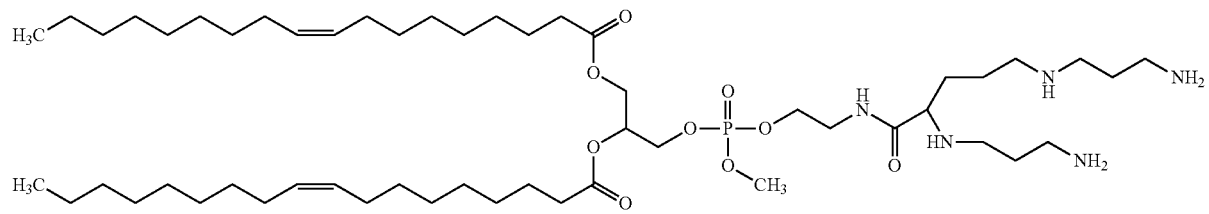
(I-1)
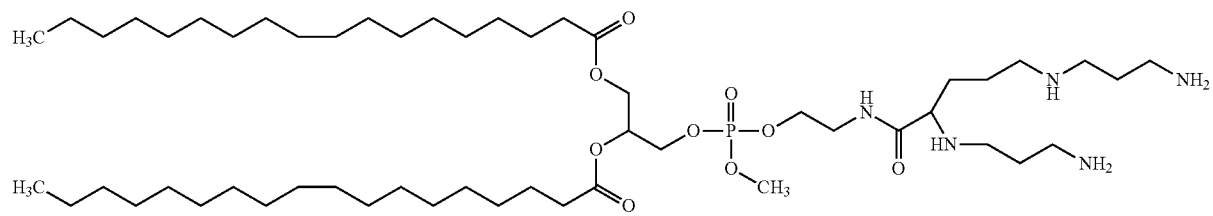
(I-2)
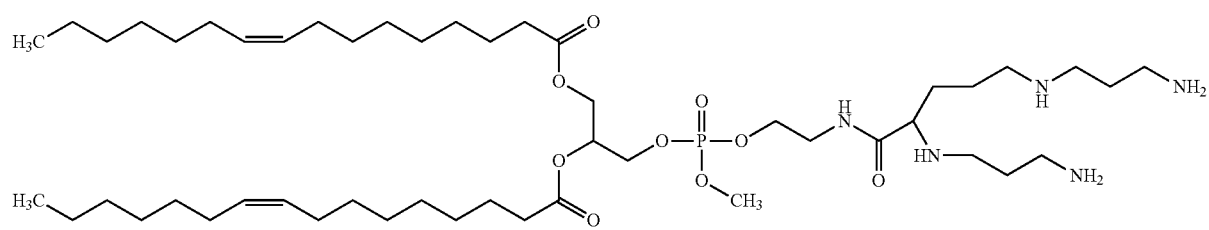
(I-3)
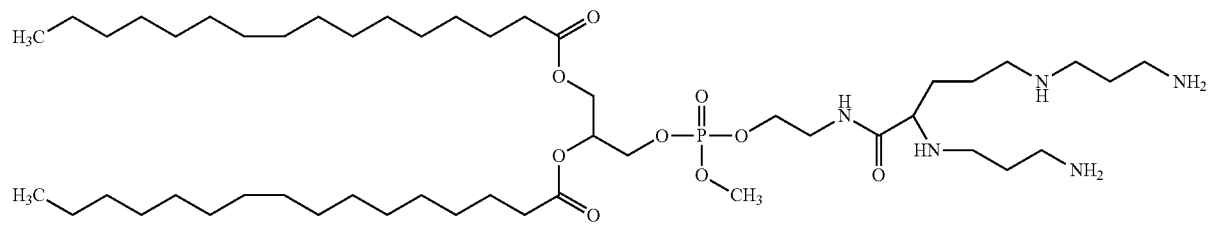
(I-4)
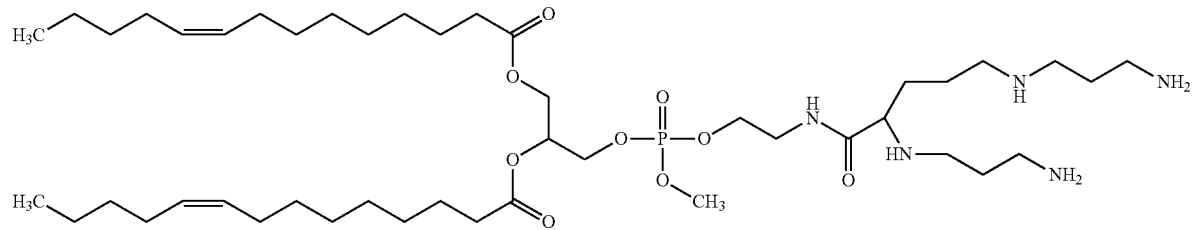
(I-5)
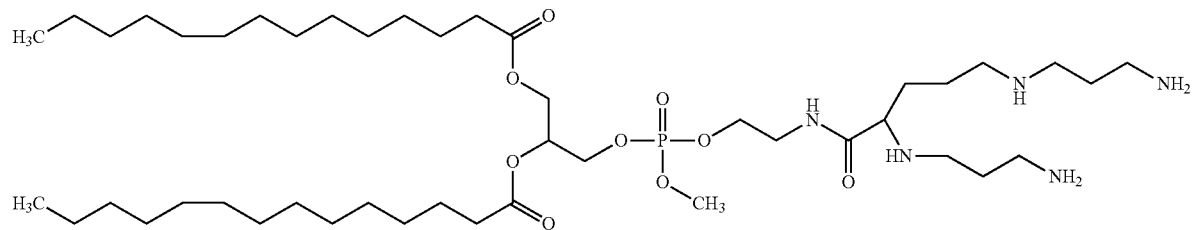
(I-6)

(I-7)
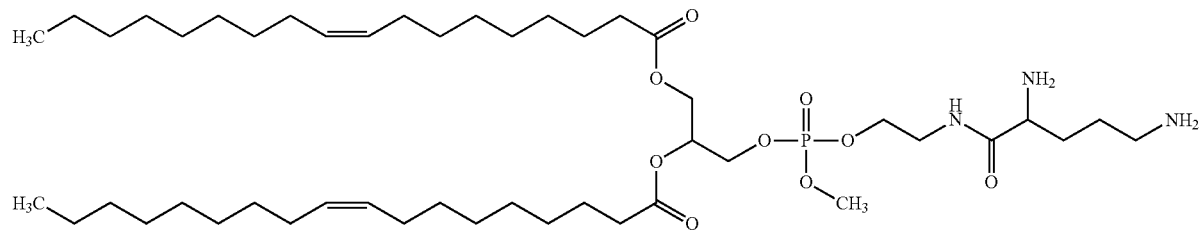
(I-8)
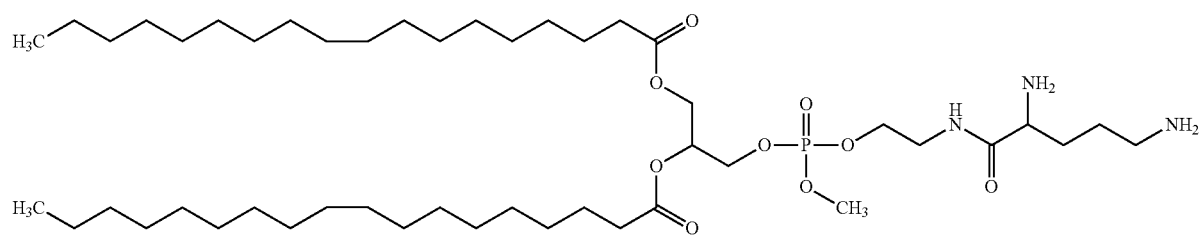
(I-9)
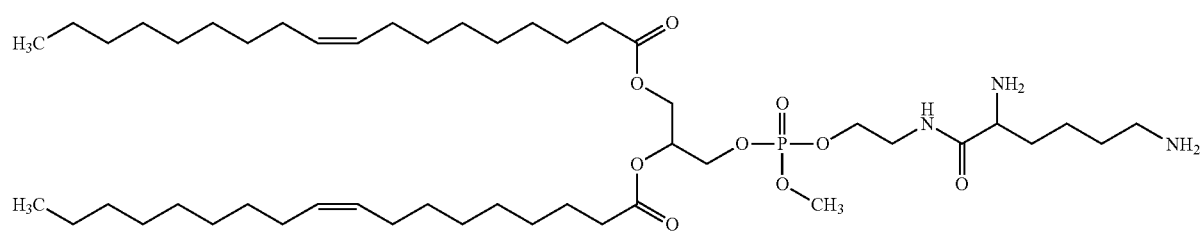
(I-10)
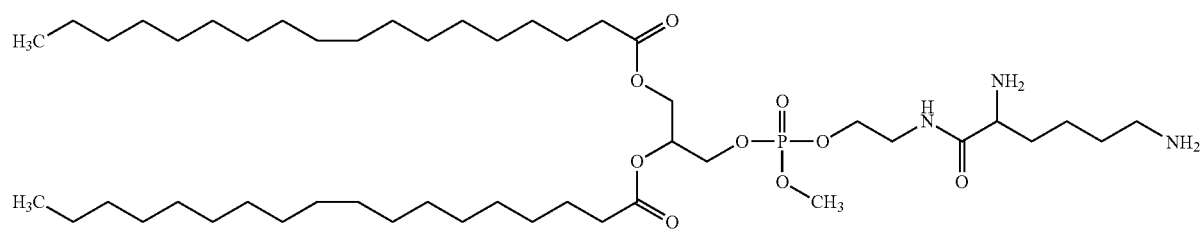
(I-11)
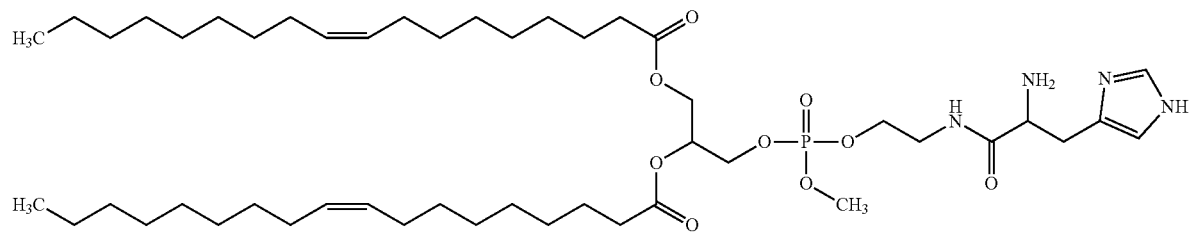
(I-12)
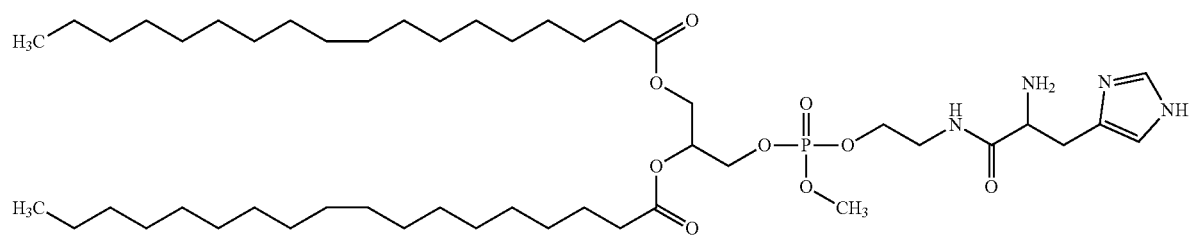

(I-13)

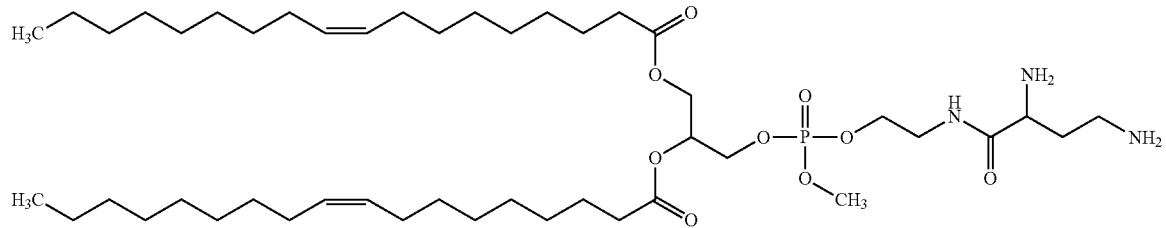

(I-14)

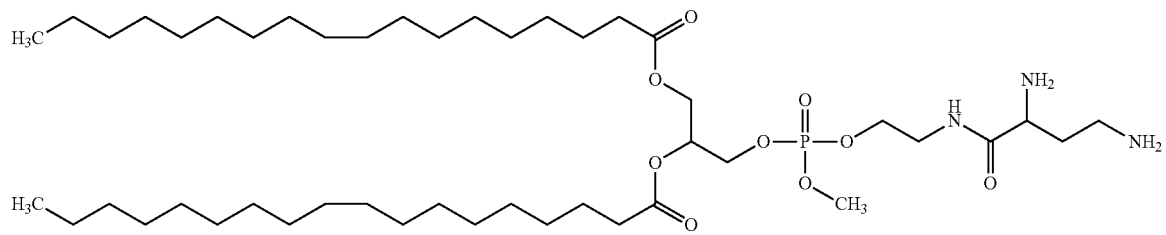

In another embodiment, the disclosure provides compositions of a compound of Formula I and at least one or more neutral lipids.

In another aspect, the disclosure provides compositions of a compound of Formula I and at least one or more neutral lipids, wherein the one or more neutral lipids is selected from DOPE, DPhPE, cholesterol, DOPC, Lyso-PE (1-acyl-2-hydroxy-sn-glycero-3-phospho-ethanolamine), Lyso-PC (1-acyl-3-hydroxy-sn-glycero-3-phosphocholine), and 3-alkoxy-2-hydroxy-1-acetamidopropane In another embodiment, the disclosure provides compositions of a compound of Formula I, and at least one or more cationic lipids, and/or at least one or more neutral lipids.

In another aspect, the disclosure provides compositions of a compound of Formula I, and at least one or more cationic lipids, and/or at least one or more neutral lipids, wherein the cationic lipid is selected from GeneIn™, LipofectAmine™ 2000, LipofectAmine™, Lipofectin®, DMRIE-C, CellFectin® (Invitrogen), Oligofectamine® (Invitrogen), LipofectAce® (Invitrogen), Fugene® (Roche, Basel, Switzerland), Fugene® HD (Roche), Transfectam® (Tranfectam, Promega, Madison, WI), Tfx-10® (Promega), Tfx-20® (Promega), Tfx-50® (Promega), Transfectin™ (BioRad, Hercules, CA), SilentFect™ (Bio-Rad), Effectene® (Qiagen, Valencia, CA), DC-chol (Avanti Polar Lipids), GenePorter® (Gene Therapy Systems, San Diego, CA), DharmaFect 1® (Dharmacon, Lafayette, CO), DharmaFect 2® (Dharmacon), DharmaFect 3®(Dharmacon), DharmaFect 4® (Dharmacon), Escort™ III (Sigma, St. Louis, MO), Escort™ IV (Sigma), DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyloxypropyl)-2-hydroxy-propane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyl-oxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)-propane-1,3-diamine, N-1-dimethyl-N-1-(2,3-diapalmityloxypropyl)-2-(3-amino-2-hydroxypropyloxy)-propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-β-hydroxyethylamine), L-Lysine-bis(O,O'-oleoyl-β-hydroxy-ethyl)amide dihydrochloride, L-Lysine-bis-(O,O'-palmitoyl-β-hydroxyethyl)amide dihydrochloride, 1,4-bis[(3-(3-aminopropyl)-alkylamino)-2-hydroxypropyl)piperazine, L-Lysine-bis-(O,O'-myristoyl-β-hydroxyethyl)amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis[(3-(3-aminopropyl)-oleylamino)-2-hydroxypropyl]piperazine, L-Ornithine-bis-(O,O'-palmitoyl-β-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]-piperazine, L-Arginine-bis-(O,O'-oleoyl-β-hydroxyethyl)amide dihydrochloride, bis[(3-(3-aminopropyl)-myristylamino)2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)-amide dihydrochloride, 1,4-bis[(3-(3-aminopropyl)-palmitylamino)-2-hydroxypropyl]piperazine, Glycine-bis-(O,O'-palmitoyl-β-hydroxyethyl)amide dihydrochloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethyl-ammonium iodide, 1,4-bis[(3-myristylamino)propyl]-piperazine, 1-dimethylamino-3-trimethyl-ammonio-DL-2-propyl-cholesteryl carboxylate iodide, cholesteryl-3β-carboxyamidoethylene-amine, cholesteryl-3β-oxysuccinamido-ethylenetrimethylammonium iodide, 1-dimethylamino-3-trimethylammonio-DL-2-propyl-cholesteryl-3β-oxysuccinate iodide, 2-[(2-trimethylammonio)-ethylmethyl-amino]ethyl-cholesteryl-3β-oxysuccinate iodide, 3β[N—(N', N'-dimethylamino-ethane)carbamoyl]cholesterol, and 3β-[N-(polyethyleneimine)-carbamoyl] cholesterol, 1,4-bis[(3-palmitylamino)propyl] piperazine, L-Ornithylglycyl-N-(1-heptadecyloctadecyl)-glycinamide, $N^2,N^5$-Bis(3-aminopropyl)-L-ornithylglycyl-N-(1-heptadecyloctadecyl)-glycin-amide, 1,4-bis[(3-(3-amino-2-hydroxypropyl)-alkylamino)-2-hydroxypropyl]-piperazine, $N^2$—[$N^2,N^5$-Bis(3-aminopropyl)-L-ornithyl]-N, N-dioctadecyl-L-glutamine, $N^2$—[$N^2$,$N^5$-Bis(amino-propyl)-L-ornithyl]-N-N-dioctadecyl-L-α-glutamine, 1,4-bis[(3-(3-amino-2-hydroxy-propyl)-oleylamino)2-hydroxypropyl]piperazine, $N^2$—[$N^2$,$N^5$-Bis(amino-propyl)-L-ornithyl]-N-N-dioctadecyl-L-α-asparagine, N—[$N^2$—[$N^2$,$N^5$-Bis[(1,1-dimethyl-ethoxy)carbonyl]-$N^2$,$N^5$-bis[3-[(1,1-dimethylethoxy)carbonyl]aminopropyl]-L-ornithyl-N-N-dioctadecyl-L-glutaminyl]-L-glutamic acid, $N^2$—[$N^2$,$N^5$-Bis(3-aminopropyl)-L-ornithyl]-N,N-diolyl-L-glutamine, $N^2$—[$N^2$,$N^5$-Bis(aminopropyl)-L-ornithyl]-N-N-dioleyl-L-α-glutamine, 4-bis[(3-(3-amino-2-hydoxypropyl)-myristylamino)-2-hydroxy-propyl]piperazine, $N^2$—[$N^2$,$N^5$-Bis(aminopropyl)-L-ornithyl]-N-N-dioleyl-L-α-asparagine, N—[$N^2$—[$N^2$,$N^5$-Bis[(1,1-dimethyl ethoxy)carbonyl]-$N^2$,$N^5$-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2$,$N^5$-Bis(3-aminopropyl)-L-ornithyl]-N,N-dipalmityl-L-glutamine, $N^2$—[$N^2$,$N^5$-Bis(amino-propyl)-L-ornithyl]-N—N-dipalmityl-L-α-glutamine, $N^2$—[$N^2$,$N^5$-Bis(aminopropyl)-L-ornithyl]-N—N-dipalmityl-L-α-asparagine, N—[$N^2$—[$N^2$,$N^5$-Bis[(1,1-dimethylethoxy)-carbonyl]-$N^2$,$N^5$-bis[3-[(1,1-dimethyl-ethoxy)carbonyl]aminopropyl]-L-ornithyl-N—N-dipalmityl-L-glutaminyl]-L-glutamic acid, $N^2$—[$N^2$,$N^5$-Bis(3-aminopropyl)-L-ornithyl]-N,N-dimyristyl-L-glutamine, $N^2$—[$N^2$, $N^5$—Bis(amino-propyl)-L-ornithyl]-N-N-dimyristyl-L-α-glutamine, $N^2$—[$N^2$,$N^5$-Bis(aminopropyl)-L-ornithyl]-N-N-dimyristyl-L-α-asparagine, 1,4-bis[(3-(3-amino-2-hydroxypropyl)-palmityl-amino)-2-hydroxypropyl]-piperazine, N—[$N^2$—[$N^2$,$N^5$-Bis[(1,1-di methyl ethoxy)carbonyl]-$N^2$, $N^5$-bis[3-[(1,1-dimethylethoxy)carbonyl]aminopropyl]-L-ornithyl-N—N-dimyristyl-L-glutaminyl]-L-glutamic acid, 1,4-bis[(3-(3-aminopropyl)-myristylamino)propyl]piperazine, $N^2$—[$N^2$,$N^5$-Bis(3-amino-propyl)-L-ornithyl]-N,N-dilaureyl-L-glutamine, $N^2$—[$N^2$,$N^5$-Bis(amino-propyl)-L-ornithyl]-N—N-dilaureyl-L-α-glutamine, $N^2$—[$N^2$, $N^5$—Bis(aminopropyl)-L-ornithyl]-N—N-dilaureyl-L-α-asparagine, N—[$N^2$—[$N^2$,$N^5$-Bis[(1,1-dimethylethoxy)-carbonyl]-$N^2$, $N^5$-bis[3-[(1,1-dimethyl-ethoxy)carbonyl]aminopropyl]-L-ornithyl-N—N-dilaureyl-L-glutaminyl]-L-glutamic acid, 3-[N',N''-bis(2-tertbutyloxycarbonyl-amino-ethyl)guanidino]-N,N-dioctadec-9-enyl-propionamide, 3-[N', N''-bis(2-tertbutyloxy-carbonylaminoethyl)guanidino]-N,N-dipalmityl-propionamide, 3-[N',N''-bis(2-tertbutyl-oxycarbonylaminoethyl)guanidino]-N,N-dimyristyl-propionamide, 1,4-bis[(3-(3-amino-propyl)-palmitylamino)propyl]piperazine, 1,4-bis[(3-(3-amino-2-hydroxy-propyl)-oleyl-amino)propyl]piperazine, N,N-(2-hydroxy-3-aminopropyl)-N-2-hydroxypropyl-3-N,N-diolylaminopropane, N,N-(2-hydroxy-3-amino-propyl)-N-2-hydroxy-propyl-3-N,N-dipalmitylaminopropane, N,N-(2-hydroxy-3-amino-propyl)-N-2-hydroxypropyl-3-N,N-dimyristylaminopropane, 1,4-bis[(3-(3-amino-2-hydroxypropyl)-myristylamino)-propyl]-piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylamino-propane, palmitoyl-2-hydroxy-3-N,N-dimethy-amino propane, 1,2-dipalmitoyl-1-N,N-dimethylamino-propane, myristoyl-2-hydroxy-3-N,N-dimethyamino propane, 1,2-dimyristoyl-1-N,N-dimethylaminopropane, (3-Amino-propyl)-→4-(3-amino-propylamino)-4-tetradecyl-carbamoyl-butylcarbamic acid cholestryl ester, (3-Amino-propyl)-→4-(3-amino-propylamino-4-carbamoylbutylcarbamic acid cholestryl ester, (3-Amino-propyl)-→4-(3-amino-propylamino)-4-(2-dimethylamino-ethylcarbamoyl)-butylcarbamic acid cholesteryl ester, Spermine-5-carboxyglycine (N'-stearyl-N'-oleyl) amide tetratrifluoro-acetic acid salt, Spermine-5-carboxyglycine (N'-stearyl-N'-elaidyl) amide tetratri-fluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxy-propyl)-palmityl-amino)-propyl]-piperazine, N-(3-aminopropyl)-N,N'-bis-(dodecyloxyethyl)-piperazinium bromide, N-(3-amino-propyl)-N,N'-bis-(oleyloxyethyl)-piperazinium bromide, N-(3-aminopropyl)-N,N'-bis-(palmityl-oxyethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N',-methyl-N,N'-(bis-2-oleyl-oxyethyl)-piperazinium bromide, N-(3-aminopropyl)-N'-methyl-N,N'-(bis-2-palmityloxyethyl)-piperazinium bromide, N-(3-amino-propyl)-N'-methyl-N,N'-(bis-2-myristyloxyethyl)-piperazinium bromide, 1,4-bis[(3-(3-amino-propyl)-oleylamino)-2-hydroxy-propyl]piperazine, 1,4-bis[(3-(3-aminopropyl)-myristylamino)-2-hydroxy-propyl] piperazine, or 1,4-bis[(3-(3-aminopropyl)-palmitylamino)-2-hydroxy-propyl]-piperazine, 2,3-dioleyloxy-1,4-N,N'-dimethyl-N,N'-di(2-hydroxy-3-aminopropyl)-diamino-butane, 2,3-dipalmitoleoyloxy-1,4-N,N-dimethyl-N,N'-di (2-hydroxy-3-amino-propyl)-diamino-butane, 2,3-dimyristoleoyloxy-1,4-N,N'-dimethyl-N,N'-di(2-hydroxy-3-aminopropyl)-diamino-butane, 2,3-dioleyloxy-1,4-N,N'-dimethyl-N,N'-di(3-amino-propyl)-diaminobutane, 2,3-dipalmitoleoyloxy-1,4-N,N'-dimethyl-N,N'-di(3-amino-propyl)-diaminobutane, 2,3-dimyristoleoyloxy-1,4-N,N'-dimethyl-N,N'-di(3-amino-propyl)-diaminobutane, 2,3-dioleyloxy-1,4-N,N'-dimethyl-N,N'-di(5-carboxamido-spermine)-diamino-butane, 2,3-dipalmitoleoyloxy-1,4-N,N'-dimethyl-N,N'-di(5-carboxamidospermine)-diamino-butane, 2,3-dimyristoleoyloxy-1,4-N,N'-dimethyl-N,N'-di (5-caqrboxamidospermine)-diaminobutane, 2,3-dioleyloxy-1,4-N,N'-dimethyl-N,N'-di(lysyl)-diaminobutane, 2,3-dipalmitoleoyloxy-1,4-N,N'-di methyl-N,N'-di(lysyl)-diamino-butane, 2,3-dimyristoleoyloxy-1,4-N,N'-dimethyl-N,N'-di(lysyl)-diaminobutane, 2,3-dioleyloxy-1,4-N,N'-dimethyl-N,N'-di(histidyl)-diaminobutane, 2,3-dipalmitoleoyl-oxy-1,4-N,N'-dimethyl-N,N'-di(histidyl)-diaminobutane, 2,3-dimyristoleoyloxy-1,4-N,N'-dimethyl-N,N'-di(histidyl)-diaminobutane, 2,3-dioleyloxy-N,N-dimethyl-1,4-diaminobutane, 2,3-dipalmitoleoyloxy-N,N-dimethyl-1,4-diaminobutane, 2,3-dimyrist-oleoyloxy-N,N'-dimethyl-1,4-diaminobutane; PAMAM dendrimers, $NH_3$ core dendrimers, ethylenediamine core dendrimers, polyethylene-imine, and polyethylenimine conjugates.

In another aspect, the disclosure provides compositions of a compound of Formula I, and at least one or more cationic lipids, and/or at least one or more neutral lipids, wherein the one or more neutral lipids is selected from DOPE, DPhPE, cholesterol, DOPC, Lyso-PE (1-acyl-2-hydroxy-sn-glycero-3-phospho-ethanolamine), Lyso-PC (1-acyl-3-hydroxy-sn-glycero-3-phosphocholine), and 3-alkoxy-2-hydroxy-1-acetamidopropane.

In another embodiment, the disclosure provides compositions of a compound of Formula I, and one or more polyamine transfection agents.

In another aspect, the disclosure provides compositions of a compound of Formula I, and one or more polyamine transfection agents, wherein the one or more polyamine transfection agents is selected from dense star dendrimers, PAMAM dendrimers, NFE core dendrimers, ethylenediamine core dendrimers, dendrimers of generation 5 or higher, dendrimers with substituted groups, dendrimers comprising one or more amino acids, grafted dendrimers, activated dendrimers, polyethylenimine, polyethylenimine conjugates, polylysine, poly arginine, polyorinthine and histone.

In another embodiment, the disclosure provides compositions of a compound of Formula I, and one or more fusion agents.

In another aspect, the disclosure provides compositions of a compound of Formula I, and one or more fusion agents, wherein the one or more fusion agents includes a polycationic nucleic acid binding moiety.

In another aspect, the disclosure provides compositions of a compound of Formula I, and one or more fusion agents, further comprising one or more cationic lipids and/or one or more neutral lipids.

In another embodiment, the disclosure provides compositions of a compound of Formula I, and one or more cell surface ligands.

In another aspect, the disclosure provides compositions of a compound of Formula I, and one or more cell surface ligands, wherein the one or more cell surface ligands comprises a polycationic nucleic acid binding moiety.

In another aspect, the disclosure provides compositions of a compound of Formula I, and one or more cell surface ligands, further comprising one or more cationic lipids and/or one or more neutral lipids and/or one or more fusion agents.

In another embodiment, the disclosure provides compositions of a compound of Formula I, and one or more nuclear localization peptides or one or more protein cell surface ligands.

In another aspect, the disclosure provides compositions of a compound of Formula I, and one or more nuclear localization peptides or one or more protein cell surface ligands, wherein the one or more nuclear localization peptides or the one or more protein cell surface ligands comprises a polycationic nucleic acid binding moiety.

In another aspect, the disclosure provides compositions of a compound of Formula I, and one or more nuclear localization peptides or one or more protein cell surface ligands, further comprising one or more cationic lipids and/or one or more neutral lipids and/or one or more fusion agents and/or one or more cell surface ligands.

In another embodiment, the disclosure provides compositions of a compound of Formula I, and one or more amphipathic peptides.

In another aspect, the disclosure provides compositions of a compound of Formula I, and one or more amphipathic peptides, wherein the one or more amphipathic peptide functions as a fusion agent.

In another aspect, the disclosure provides compositions of a compound of Formula I, and one or more amphipathic peptides, wherein the one or more amphipathic peptides are selected from: FEAALAEALAEALA (SEQ ID NO: 10), Ac-LARLLPRLLARL-NHCH3 (SEQ ID NO: 11), GLLEELLELLEELWEELLEG (SEQ ID NO: 12), GWEGLIEGIEGGWEGLIEG (SEQ ID NO: 13), GLFEALAEFIEGGWEGLIEG (SEQ ID NO: 14), GLFEALLELLESLWELLLEA (SEQ ID NO: 15), GGYCLEKWMIVASELKCFGNTA (SEQ ID NO: 16), GGYCLTRWMLIEAELKCFGNTAV (SEQ ID NO: 17), and WEAALAEALAEALAEHLAEALAEALEALAA (SEQ ID NO: 18).

In another aspect, the disclosure provides compositions of a compound of Formula I, and one or more amphipathic peptides, wherein the one or more amphipathic peptides is covalently linked to a polycationic nucleic binding moiety.

In another aspect, the disclosure provides compositions of a compound of Formula I, and one or more nuclear localization peptides or one or more protein cell surface ligands, further comprising one or more cationic lipids and/or one or more neutral lipids and/or one or more fusion agents and/or one or more cell surface ligands and one/or more amphipathic peptides In another aspect, the disclosure provides compositions of a compound of Formula I, and one or more nuclear localization peptides or one or more protein cell surface ligands, further comprising one or more cationic lipids and/or one or more neutral lipids and/or one or more fusion agents and/or one or more cell surface ligands and one/or more amphipathic peptides wherein the one or more nuclear localization peptides or the one or more protein cell surface ligands comprises a polycationic nucleic acid binding moiety and wherein further the one or more amphipathic peptides are selected from: FEAALAEALAEALA (SEQ ID NO: 10), Ac-LARLLPRLLARL-NHCH3 (SEQ ID NO: 11), GLLEELLELLEELWEELLEG (SEQ ID NO: 12), GWEGLIEGIEGGWEGLIEG (SEQ ID NO: 13), GLFEALAEFIEGGWEGLIEG (SEQ ID NO: 14), GLFEALLELLESLWELLLEA (SEQ ID NO: 15), GGYCLEKWMIVASELKCFGNTA (SEQ ID NO: 16), GGYCLTRWMLIEAELKCFGNTAV (SEQ ID NO: 17), and WEAALAEALAEALAEHLAEALAEALEALAA (SEQ ID NO: 18).

In another aspect, the disclosure provides compositions of a compound of Formula I, and/or one or more neutral lipids and/or one or more cationic lipids and one or more of the following peptides: GYSTPPKKKRKVEDP (SEQ ID NO:1), GYSTPPKTRRRP (SEQ ID NO:2), GYSTPGRKKR (SEQ ID NO:3), GYSTPRRNRRRRW (SEQ ID NO:4), PDEVKRKKKPPTSYG (SEQ ID NO:5), PRRRTKPPTSYG (SEQ ID NO:6), RKKRGPTSYG (SEQ ID NO:7), WRRRRNRRPTSYG (SEQ ID NO:8), GYGPPKKKRKVEAPYKA(K)$_{8-40}$K (SEQ ID NO:9), FEAALAEALAEALA (SEQ ID NO: 10), Ac-LARLLPRLLARL-NHCH3 (SEQ ID NO: 11), GLLEELLELLEELWEELLEG (SEQ ID NO: 12), GWEGLIEGIEGGWEGLIEG (SEQ ID NO: 13), GLFEALAEFIEGGWEGLIEG (SEQ ID NO: 14), GLFEALLELLESLWELLLEA (SEQ ID NO: 15), GGYCLEKWMIVASELKCFGNTA (SEQ ID NO: 16), GGYCLTRWMLIEAELKCFGNTAV (SEQ ID NO: 17), WEAALAEALAEALAEHLAEALAEALEALAA (SEQ ID NO: 18), INIGTTGWGDHYSLY (SEQ ID NO: 19), AARSPSYYRYDYGPYYAMDYD (SEQ ID NO:20), GKWERKPIRCAS (SEQ ID NO:31), GACSERSMNFCG (SEQ ID NO:21), GACYGLPHKFCG (SEQ ID NO:22), YYCQQRSSYPYTFGG (SEQ ID NO:23), TRQARRNRRRRWRERQRGSGSG (SEQ ID NO:24), RDWSSQHPGRCNGETHLK (SEQ ID NO:25), GGGDYYCAAWDDSLNGYSVF (SEQ ID NO:26), VIVTGGDYSFALPVGQWPVMTGGA (SEQ ID NO:27), DKPSYQFGGHNSVDFEEDTLPKV (SEQ ID NO:28), HLRRLRRRLLREAEG (SEQ ID NO:29), and YYCARSGYYAMDYWGQGT (SEQ ID NO:30). In some embodiments, the above-mentioned peptides are covalently linked to a nucleic acid binding moiety.

In another embodiment, the disclosure provides compositions of a compound of Formula I, further comprising one or more nucleic acids.

In another embodiment, the disclosure provides compositions of a compound of Formula I, further comprising one or more nucleic acids, wherein the one or more nucleic acids are selected from DNA and RNA.

In another embodiment, the disclosure provides compositions of a compound of Formula I, further comprising one or more nucleic acids, wherein the one or more nucleic acids are selected from DNA and RNA, wherein the RNA is and RNAi molecule.

In another embodiment, the disclosure provides methods for introducing a nucleic acid, protein, or peptide into a eukaryotic cell, comprising contacting the cell with a composition of any of the disclosed compositions, thereby introducing the nucleic acid, protein, or peptide into the cell.

In another embodiment, the disclosure provides methods for introducing a nucleic acid, protein, or peptide into a eukaryotic cell, wherein the cell is a human cell, comprising contacting the cell with a composition of any of the disclosed compositions, thereby introducing the nucleic acid, protein, or peptide into the cell.

In another embodiment, the disclosure provides methods for introducing a nucleic acid, protein, or peptide into a eukaryotic cell, wherein the cell is an animal cell, comprising contacting the cell with a composition of any of the disclosed compositions, thereby introducing the nucleic acid, protein, or peptide into the cell.

In another embodiment, the disclosure provides kits including a compound of Formula I, and one or more cationic lipids, and/or one or more neutral lipids, and/or one or more cell surface ligands, and/or one or more fusion agents, and/or one or more nuclear localization peptides or proteins and/or one or more amphipathic peptides.

In another embodiment, the disclosure provides methods for expressing a protein in a cell, comprising contacting the cell with an expression vector encoding the protein and a compound of Formula I, as described herein, or the composition of any the disclosed compositions.

In another embodiment, the disclosure provides methods for inhibiting expression of a protein in a cell, comprising contacting the cell with an RNAi molecule and a compound of Formula I, as described herein, or the composition of any one of the disclosed compositions.

The skilled artisan will recognize that, although the compounds of the invention are shown here for convenience in their neutral (unprotonated) forms, these compounds may also exist in a partially or fully protonated form in solutions of appropriate pH, and that the present invention encompasses the compounds in all their protonated, unprotonated, ionized and non-ionized forms without limitation, unless specifically indicated otherwise.

Preparation of the Compounds of Formula I

The compounds of Formula I may be synthesized using methods that are well known in the art, as shown for example, in Schemes I and II.

SCHEME I

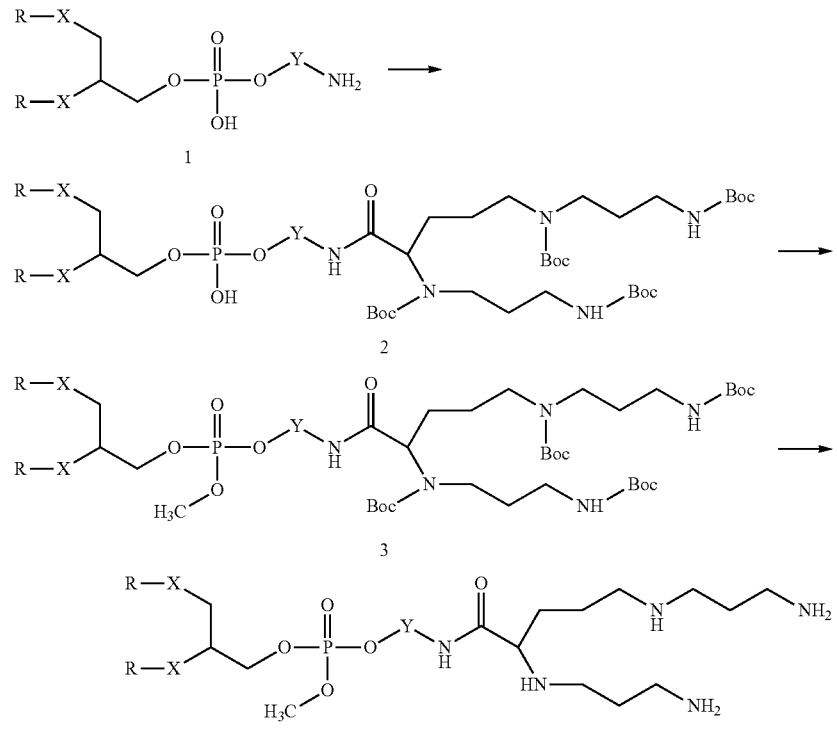

Thus, in one embodiment, compound 4 has formula 4a-4e as shown below:

| Compound | R | X | Y |
|---|---|---|---|
| 4a | —OC(O)(CH$_2$)$_7$CH═CH(CH$_2$)$_7$CH$_3$ (cis) | —C(O)O— | —CH$_2$CH$_2$— |
| 4b | —OC(O)(CH$_2$)$_7$CH═CH(CH$_2$)$_5$CH$_3$ (cis) | —C(O)O— | —CH$_2$CH$_2$— |
| 4c | —OC(O)(CH$_2$)$_{14}$CH$_3$ | —C(O)O— | —CH$_2$CH$_2$— |
| 4d | —OC(O)(CH$_2$)$_7$CH═CH(CH$_2$)$_3$CH$_3$ (cis) | —C(O)O— | —CH$_2$CH$_2$— |
| 4e | —OC(O)(CH$_2$)$_{12}$CH$_3$ | —C(O)O— | —CH$_2$CH$_2$— |

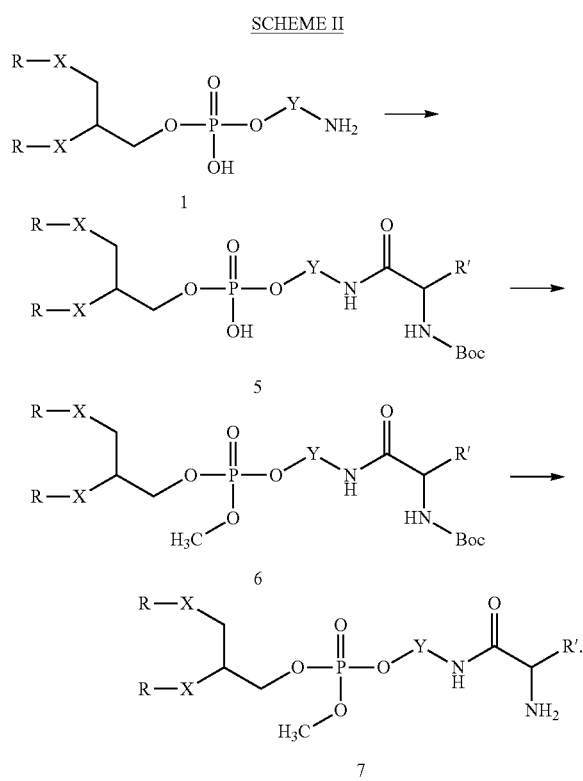

SCHEME II

| Compound | R (cis) | X | Y | R' |
|---|---|---|---|---|
| 7a | —OC(O)(CH$_2$)$_7$CH═CH(CH$_2$)$_7$CH$_3$ | —C(O)O— | —CH$_2$CH$_2$— | —(CH$_2$)$_4$NH$_2$ |
| 7b | —OC(O)(CH$_2$)$_7$CH═CH(CH$_2$)$_7$CH$_3$ | —C(O)O— | —CH$_2$CH$_2$— | —CH$_2$(C$_3$H$_3$N$_2$) |
| 7c | —OC(O)(CH$_2$)$_7$CH═CH(CH$_2$)$_7$CH$_3$ | —C(O)O— | —CH$_2$CH$_2$— | —(CH$_2$)$_3$NH$_2$ |
| 7d | —OC(O)(CH$_2$)$_7$CH═CH(CH$_2$)$_7$CH$_3$ | —C(O)O— | —CH$_2$CH$_2$— | —CH$_2$CH$_2$NH$_2$ |

As shown in Scheme I, the phosphatidylethanol-amine analog (1) may be condensed with BOC protected carboxyspermine with the aid of a N,N-diisopropylcarbodiimide to obtain the product (2). The phosphate on the adduct (2) may be alkylated with methyltriflate to provide the alkylated product (3) and the BOC protecting group may be removed with TFA to obtain the desired compounds (4a-e). Scheme II demonstrates that compounds (7a-d) may be synthesized in a similar fashion starting with the desired amino acid.

Formulation and Use of Compounds of Formula I for Transfection

The lipids described above may be formulated by various methods to be used in transfection. One of the simplest methods for formulation is reverse evaporation. In this procedure the required amount of the cationic lipid and a co-lipid (if used, e.g. a neutral lipid) are dissolved in chloroform or other appropriate organic solvent and are transferred into a round bottom flask. Enough molecular biology grade water is added to make the desired concentration of total lipids/volume (e.g. 2 mg/ml) and the chloroform is then removed under vacuum (e.g. on a rotary evaporator). As the chloroform is removed liposomes are formed in the aqueous medium. Other methods for formulation that can be used are sonication and microfluidization. In both cases the required amount of the cationic lipid and the co-lipid in a chloroform (or other organic solvent) are transferred into a flask. The chloroform is evaporated to leave a thin film of lipid mixture in the flask. The lipid film is then hydrated with molecular biology grade water to make the desired concentration and sonicated or microfluidized. In another case of formulation, the chloroform is evaporated to leave a thin film of lipid mixture in the flask and the thin film can be dissolved in ethanol or ethanol water mixture to obtain the desired concentration. The ethanolic solution can then be used in transfection.

The new lipids are formulated with one or more co-lipids, most advantageously neutral co-lipids, although the skilled artisan will recognize that other lipids, including cationic lipids described above, may be used. For example, formulations where the molar ratio of cationic lipid:DOPE was varied from 3:1 to 1:16 were prepared using the above methods. Formulation of compounds having the structure 4 above were prepared where the hydrocarbon chain was varied from $C_{14}$-$C_{18}$ and the histidine, lysine, ornithine and diaminobutane analogs 7a, 7b, 7c, and 7d and where the hydrocarbon chain was oleyl ($C_{18}$). More analogs of 7 where the hydrocarbon chain was varied from $C_{14}$-$C_{18}$ were also prepared and were formulated in the same manner. Other neutral lipids such as, but not limited to, DPhPE, cholesterol, DOPC, Lyso-PE (1-acyl-2-hydroxy-sn-glycero-3-phosphoethanol amine), Lyso-PC (1-acyl-3-hydroxy-sn-glycero-3-phosphocholine), and/or 3-alkoxy-2-hydroxy-1-acetamidopropane may be used in the formulation.

The new lipids may be formulated with one or more cationic lipids and/or one or more neutral lipids. The cationic lipids may be GeneIn™, LipofectAmine™ 2000, LipofectAmine™, Lipofectin®, DMRIE-C, CellFectin® (Invitrogen), Oligofectamine® (Invitrogen), LipofectAce® (Invitrogen), Fugene® (Roche, Basel, Switzerland), Fugene® HD (Roche), Transfectam® (Tranfectam, Promega, Madison, WI), Tfx-10® (Promega), Tfx-20® (Promega), Tfx-50® (Promega), Transfectin™ (BioRad, Hercules, CA), SilentFect™ (Bio-Rad), Effectene® (Qiagen, Valencia, CA), DC-chol (Avanti Polar Lipids), GenePorter® (Gene Therapy Systems, San Diego, CA), DharmaFect 1® (Dharmacon, Lafayette, CO), DharmaFect 2® (Dharmacon), DharmaFect 3® (Dharmacon), DharmaFect 4® (Dharmacon), Escort™ III (Sigma, St. Louis, MO), Escort™ IV (Sigma), DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyl-oxypropyl)-2-hydroxypropane-1,3-diamine, N-1-dimethyl-N-1-(2,3-diamyristyl-oxy-propyl)-2-hydroxypropane-1,3-diamine, N-1-dimethyl-N-1-(2,3-diapalmityl-oxypropyl)-2-hydroxy-propane-1,3-diamine, N-1-dimethyl-N-1-(2,3-diaoleoyloxypropyl)-2-(3-amino-2-hydroxy-propyloxy) propane-1,3-diamine, N-1-dimethyl-N-1-(2,3-diamyristyloxypropyl)-2-(3-amino-2-hydroxypropyloxy) propane-1,3-diamine, N-1-dimethyl-N-1-(2,3-diapalmityloxy-propyl)-2-(3-amino-2-hydroxypropyloxy) propane-1,3-diamine, L-spermine-5-carboxyl-3-(DL-1,2-dipalmitoyl-dimethylaminopropyl-β-hydroxyethyl-amine, 3,5-(N,N-di-lysyl)-diamino-benzoyl-glycyl-3-(DL-1,2-dipalmitoyl-dimethylaminopropyl-β-hydroxyethylamine), L-Lysine-bis(O,O'-oleoyl-β-hydroxyethyl)amide dihydrochloride, L-Lysine-bis-(O,O'-palmitoyl-β-hydroxyethyl)-amide dihydrochloride, 1,4-bis[(3-(3-aminopropyl)-alkylamino)-2-hydroxy-propyl)piperazine, L-Lysine-bis-(O,O'-myristoyl-β-hydroxyethyl)amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis[(3-(3-aminopropyl)-oleylamino)-2-hydroxy-propyl]-piperazine, L-Ornithine-bis-(O,O'-palmitoyl-β-hydroxyethyl)-amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxy-propyl)-myristyl-amino]-butane-2,3-diol, 1,4-bis[(3-oleylamino)propyl]piperazine, L-Arginine-bis-(O,O'-oleoyl-β-hydroxyethyl)-amide dihydrochloride, bis[(3-(3-aminopropyl)-myristylamino)2-hydroxy-propyl]piperazine, L-Arginine-bis-(O,O'-palmitoyl-β-hydroxy-ethyl)-amide dihydrochloride, L-Serine-bis-(O,O'-oleoyl-β-hydroxyethyl)amide dihydrochloride, 1,4-bis[(3-(3-aminopropyl)-palmitylamino)-2-hydroxy-propyl]piperazine, Glycine-bis-(O,O'-palmitoyl-β-hydroxy-ethyl)amide dihydrochloride, Sarcosine-bis-(O,O'-palmitoyl-β-hydroxy-ethyl)amide dihydro-chloride, L-Histidine-bis-(O,O'-palmitoyl-β-hydroxyethyl)amide dihydro-chloride, cholesteryl-3β-carboxyl-amidoethylene-trimethylammonium iodide, 1,4-bis [(3-myristyl-amino)propyl]-piperazine, 1-dimethylamino-3-trimethylammonio-DL-2-propyl-cholesteryl carboxylate iodide, cholesteryl-3β-carboxy-amidoethyleneamine, cholesteryl-3β-oxysuccinamido-ethylenetrimethyl-ammonium iodide, 1-dimethylamino-3-trimethylammonio-DL-2-propyl-cholesteryl-3β-oxysuccinate iodide, 2-[(2-trimethylammonio)-ethylmethylamino] ethyl-cholesteryl-3β-oxy succinate iodide, 3β[N—(N',N'-dimethyl-aminoethane)-carbamoyl]cholesterol, and 3β-[N-(polyethylene-imine)-carbamoyl] cholesterol, 1,4-bis[(3-palmitylamino)propyl] piperazine, L-Ornithylglycyl-N-(1-heptadecyl-octadecyl) glycinamide, $N^2,N^5$-Bis(3-aminopropyl)-L-ornithylglycyl-N-(1-hepta-decyl-octadecyl)glycinamide, 1,4-bis[(3-(3-amino-2-hydroxypropyl)-alkylamino)-2-hydroxy-propyl] piperazine $N^2$—[$N^2,N^5$-Bis(3-aminopropyl)-L-ornithyl]-N,N-dioctadecyl-L-glutamine,$N^2$—[$N^2,N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl] piperazine, $N^2$—[$N^2,N^5$-Bis(aminopropyl)-L-ornithyl]-N— N-dioctadecyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dioctadecyl-L-glutaminyl]-L-glutamic acid, $N^2$—[$N^2,N^5$-Bis(3-aminopropyl)-L-ornithyl]-N,N-diolyl-L-glutamine, $N^2$—[$N^2,N^5$-Bis(aminopropyl)-L-ornithyl]-N—N-dioleyl-L-α-glutamine, 4-bis[(3-(3-amino-2-hydoxypropyl)-myristylamino)-2-hydroxypropyl]piperazine, $N^2$—[$N^2$, $N^5$—Bis (amino-propyl)-L-ornithyl]-N—N-dioleyl-L-α-asparagine, N—[$N^2$—[$N^2,N^5$-Bis[(1,1-dimethylethoxy)-carbonyl]-$N^2$, $N^5$-bis[3-[(1,1-dimethyl-ethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2,N^5$-Bis(3-aminopropyl)-L-ornithyl]-N,N-dipalmityl-L-glutamine,$N^2$—[$N^2,N^5$-Bis(amino-propyl)-L-ornithyl]-N—N-dipalmityl-L-α-glutamine, $N^2$—[$N^2,N^5$-Bis(aminopropyl)-L-ornithyl]-N—N-dipalmityl-L-α-asparagine, N—[$N^2$—[$N^2,N^5$-Bis[(1,1-dimethylethoxy)carbonyl]-$N^2,N^5$-bis[3-[(1,1-dimethyl-ethoxy)carbonyl] aminopropyl]-L-ornithyl-N—N-dipalmityl-L-glutaminyl]-L-glutamic acid, $N^2$—[$N^2,N^5$-Bis(3-aminopropyl)-L-ornithyl]-N,N-dimyristyl-L-glutamine, $N^2$—[$N^2,N^5$-Bis (aminopropyl)-L-ornithyl]-N—N-dimyristyl-L-α-glutamine, $N^2$—[$N^2$, $N^5$—Bis(amino-propyl)-L-ornithyl]-N—N-dimyristyl-L-α-asparagine, 1,4-bis[(3-(3-amino-2-hydroxypropyl)-palmityl-amino)-2-hydroxypropyl] piperazine, N—[$N^2$—[$N^2,N^5$-Bis[(1,1-dimethylethoxy) carbonyl]-$N^2,N^5$-bis[3-[(1,1-dimethylethoxy)carbonyl] aminopropyl]-L-ornithyl-N—N-dimyristyl-L-glutaminyl]-L-glutamic acid, 1,4-bis[(3-(3-aminopropyl)-myristylamino)propyl]piperazine, $N^2$—[$N^2,N^5$-Bis(3-aminopropyl)-L-ornithyl]-N,N-dilaureyl-L-glutamine, $N^2$—[$N^2,N^5$-Bis(amino-propyl)-L-ornithyl]-N—N-dilaureyl-L-α-glutamine, $N^2$—[$N^2,N^5$-Bis(aminopropyl)-L-ornithyl]-N—N-dilaureyl-L-α-asparagine, N—[$N^2$—[$N^2,N^5$-Bis[(1, 1-dimethylethoxy)carbonyl]-$N^2,N^5$-bis[3-[(1,1-dimethylethoxy)carbonyl]aminopropyl]-L-ornithyl-N—N-dilaureyl-L-glutaminyl]-L-glutamic acid, 3-[N',N"-bis(2-tertbutyloxycarbonyl-amino-ethyl)guanidino]-N,N-dioctadec-9-enyl-propionamide, 3-[N',N"-bis(2-tertbutyloxy-carbonylaminoethyl)guanidino]-N,N-dipalmityl-propionamide, 3-[N',N"-bis(2-tertbutyloxycarbonylaminoethyl)guanidino]-N,N-dimyristyl-propionamide, 1,4-bis[(3-(3-aminopropyl)-palmitylamino) propyl]piperazine, 1,4-bis[(3-(3-amino-2-hydroxypropyl)-oleylamino)-propyl]piperazine, N,N-(2-hydroxy-3-aminopropyl)-N-2-hydroxypropyl-3-N,N-diolyl-aminopropane, N,N-(2-hydroxy-3-aminopropyl)-N-2-hydroxy-propyl-3-N,N-dipalmityl-aminopropane, N,N-(2-hydroxy-3-aminopropyl)-N-2-hydroxypropyl-3-N,N-dimyristyl-aminopropane, 1,4-bis[(3-(3-amino-2-hydoxypropyl)-myristylamino)-propyl]-piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethy-aminopropane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)-→4-(3-aminopropylamino)-4-tetradecylcarbamoyl-butylcarbamic acid cholestryl ester, (3-Amino-propyl)-→4-(3-amino-propyl-amino-4-carbamoylbutylcarbamic acid cholestryl ester, (3-Amino-propyl)-→4-(3-amino-propyl-amino)-4-(2-dimethylamino-ethylcarbamoyl)-butylcarbamic acid cholesteryl ester, Spermine-5-carboxyglycine (N'-stearyl-N'-oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diamino-butyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-amino-propyl)-N, N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxy-ethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-amino-propyl)-N',-methyl-N,N'-(bis-2-palmityloxyethyl)-piperazinium bromide, N-(3-aminopropyl)-N'-methyl-N,N'-(bis-2-myristyloxyethyl)-piperazinium bromide, 1,4-bis[(3-(3-aminopropyl)-oleylamino)-2-hydroxy-propyl]piperazine, 1,4-bis[(3-(3-aminopropyl)-myristylamino)-2-hydroxy-propyl]-piperazine, or 1,4-bis[(3-(3-aminopropyl)-palmitylamino)-2-hydroxy-propyl]piperazine, 2,3-dioleyloxy-1,4-N,N'-dimethyl-N,N'-di(2-hydroxy-3-aminopropyl)-diaminobutane, 2,3-dipalmit-oleoyloxy-1,4-N,N'-dimethyl-N,N'-di(2-hydroxy-3-aminopropyl)-diaminobutane, 2,3-dimyrist-oleoyloxy-1,4-N,N'-dimethyl-N,N'-di(2-hydroxy-3-aminopropyl)-diaminobutane, 2,3-dioleyl-oxy-1,4-N,N'-dimethyl-N,N'-di(3-aminopropyl)-diaminobutane, 2,3-dipalmitoleoyloxy-1,4-N,N'-dimethyl-N,N'-di(3-aminopropyl)-diaminobutane, 2,3-dimyrist-oleoyloxy-1,4-N,N'-dimethyl-N,N'-di(3-aminopropyl)-diaminobutane, 2,3-dioleyloxy-1,4-N,N'-dimethyl-N,N'-di(5-carboxamidospermine)-diaminobutane, 2,3-dipalmitoleoyloxy-1,4-N,N'-dimethyl-N,N'-di(5-carboxamidospermine)-diaminobutane, 2,3-dimyristoleoyloxy-1,4-N,N'-dimethyl-N,N'-di(5-carboxamidospermine)-diaminobutane, 2,3-dioleyloxy-1,4-N,N'-dimethyl-N,N'-di(lysyl)-diaminobutane, 2,3-dipalmitoleoyloxy-1,4-N,N'-dimethyl-N,N'-di(lysyl)-diaminobutane, 2,3-dimyristoleoyloxy-1,4-N,N'-dimethyl-N,N'-di(lysyl)-diaminobutane, 2,3-dioleyloxy-1,4-N,N'-dimethyl-N,N'-di(histidyl)-diaminobutane, 2,3-dipalmitoleoyloxy-1,4-N,N'-dimethyl-N,N'-di(histidyl)-diaminobutane, 2,3-dimyristoleoyloxy-1,4-N,N'-dimethyl-N,N'-di(histidyl)-diamino-butane, 2,3-dioleyloxy-N,N'-dimethyl-1,4-diaminobutane, 2,3-dipalmitoleoyloxy-N,N'-dimethyl-1,4-diaminobutane, 2,3-dimyristoleoyloxy-N,N'-dimethyl-1,4-diaminobutane; PAMAM dendrimers, $NH_3$ core dendrimers, ethylenediamine core dendrimers, polyethylene-imine, and polyethylenimine conjugates.

Still other formulations may include transfection enhancing agents such as a fusion agent, a cell surface ligand and/or a nuclear localization agent such as a nuclear receptor ligand peptide, Examples of transfection enhancing agents include, but are not limited to, reovirus-related fusogenic peptides, insulin, a transferrin, epidermal growth factor, fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, a arginine rich cell permeability protein, a high mobility group protein, and invasin protein, and internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, and fragments thereof.

Use of these compositions in transfection can be carried out by methods that are known in the art where the components of a transfection complex are mixed in differing orders prior to addition to a cell culture. Typically, a liposomal preparation of the lipid, with or without co-lipid is prepared, and is then mixed with a macromolecule, such as a DNA molecule or RNAi molecule to form a transfection complex. The complex is then added to a cell culture and transfection is monitored using well known methods. Additional components such as cell surface ligands, fusion agents, nuclear localization agents and the like may be added to the nucleic acid prior to admixture with the liposome, or may be added to the liposome prior to addition of nucleic acid.

Cells which can be transfected according to these methods include, but are not limited to, virtually any eukaryotic cell including primary cells, cells in culture, a passaged cell culture or a cell line, and cells in cultured tissue. Suitable cells include human cell lines and animal cell lines. The cell may be a fibroblast. The cells can be attached cells or cells in suspension (suspension cells). In certain illustrative aspects, the cells are suspension CHO-S cells and suspension 293-F cells. Other cells that may be used include, without limitation, 293, 293-S, CHO, Cos, 3T3, Hela, primary fibroblasts, A549, Be2C, SW480, CHOK1, Griptite 293, HepG2, Jurkat, LNCap, MCF-7, NIH-3T3, PC12, C6, Caco-2, COS-7, HL60, HT-1080, IMR-90, K-562, SK-BR3, PHP1, HUVEC, MJ90, NHFF, NDFF and primary neurons.

The formulations are used in a method for producing a protein which includes contacting a cell with a lipid-nucleic acid complex as described above, where the nucleic acid encodes the protein. The cells are incubated to produce the protein and the protein is collected. Cells which can be used for protein production are described above. In addition, any composition which includes a lipid of Formula 4 or 7 can be used for transfection of cells. Such compositions are further discussed herein, and include, but are not limited to compositions comprising lipids of Formula 4 or 7, a co-lipid and an optional transfection enhancing agent such as a fusogenic peptide or protein.

Figure 2:
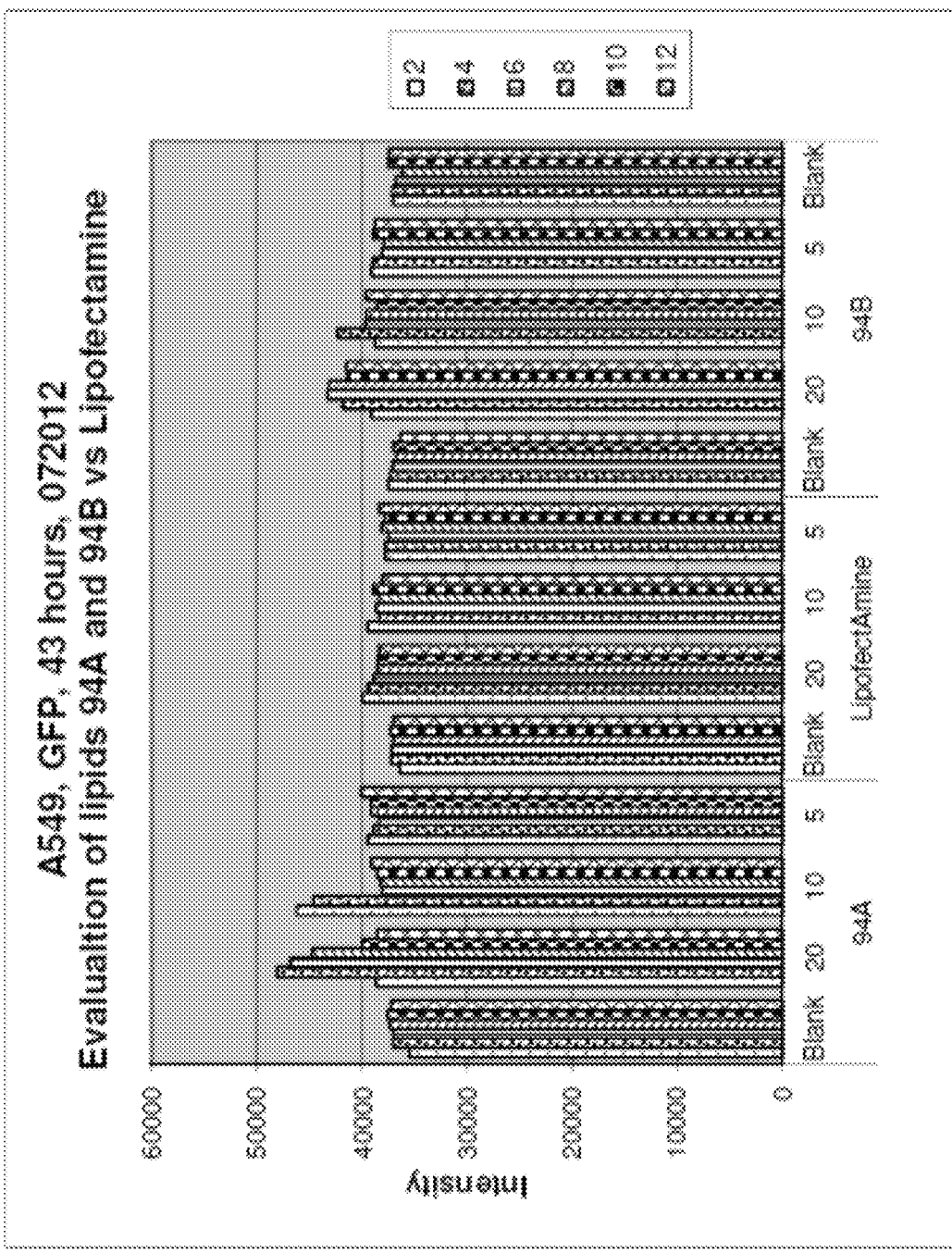
FIG. 2 shows the transfection evaluation of lipids 94-a and 94-b in A549 cells. The delivery and expression of the plasmid CMV•GFP in A549 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 3:
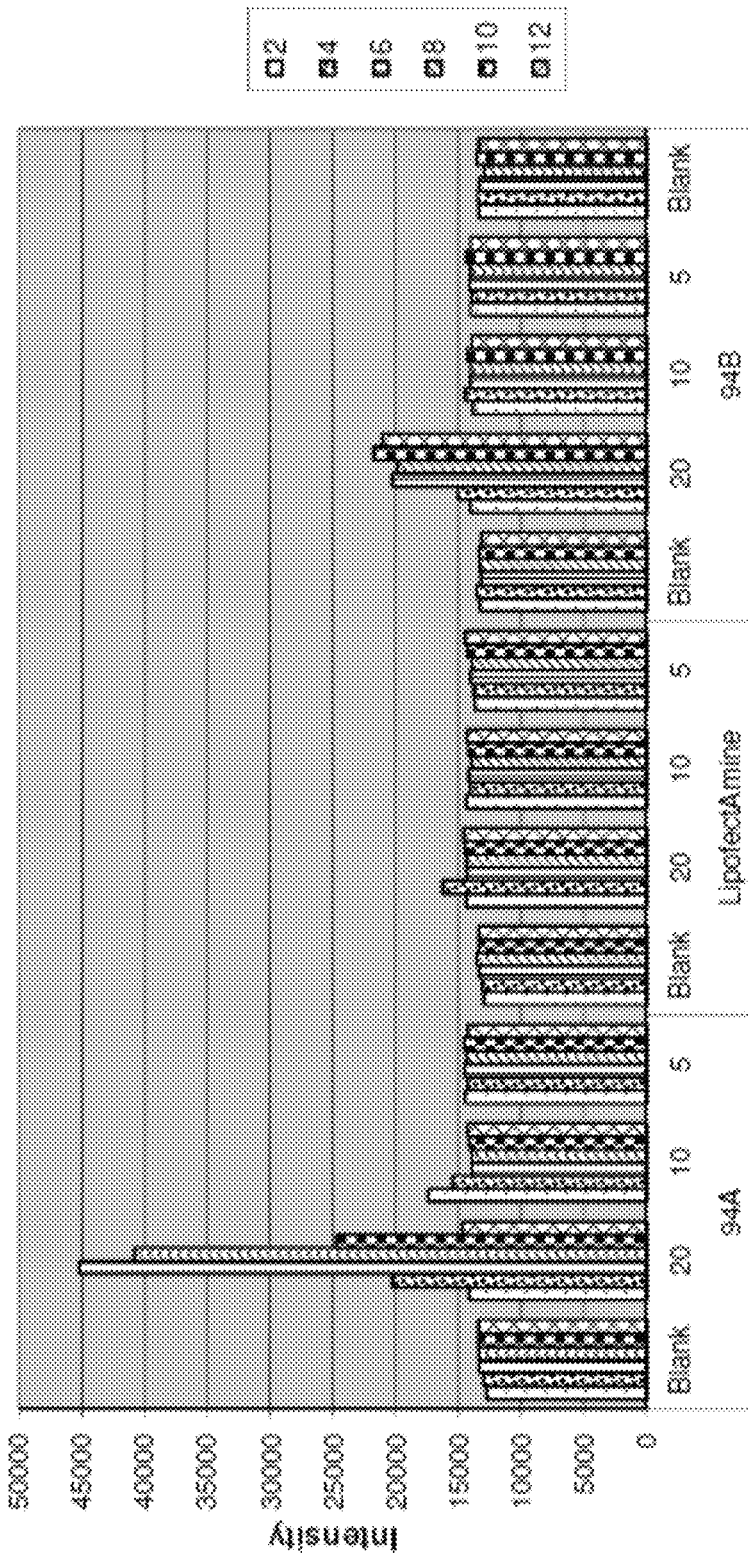
FIG. 3 shows the transfection evaluation of lipids 94-a and 94-b in CHO-K1 cells. The delivery and expression of the plasmid CMV•GFP in CHO-K1 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 4:
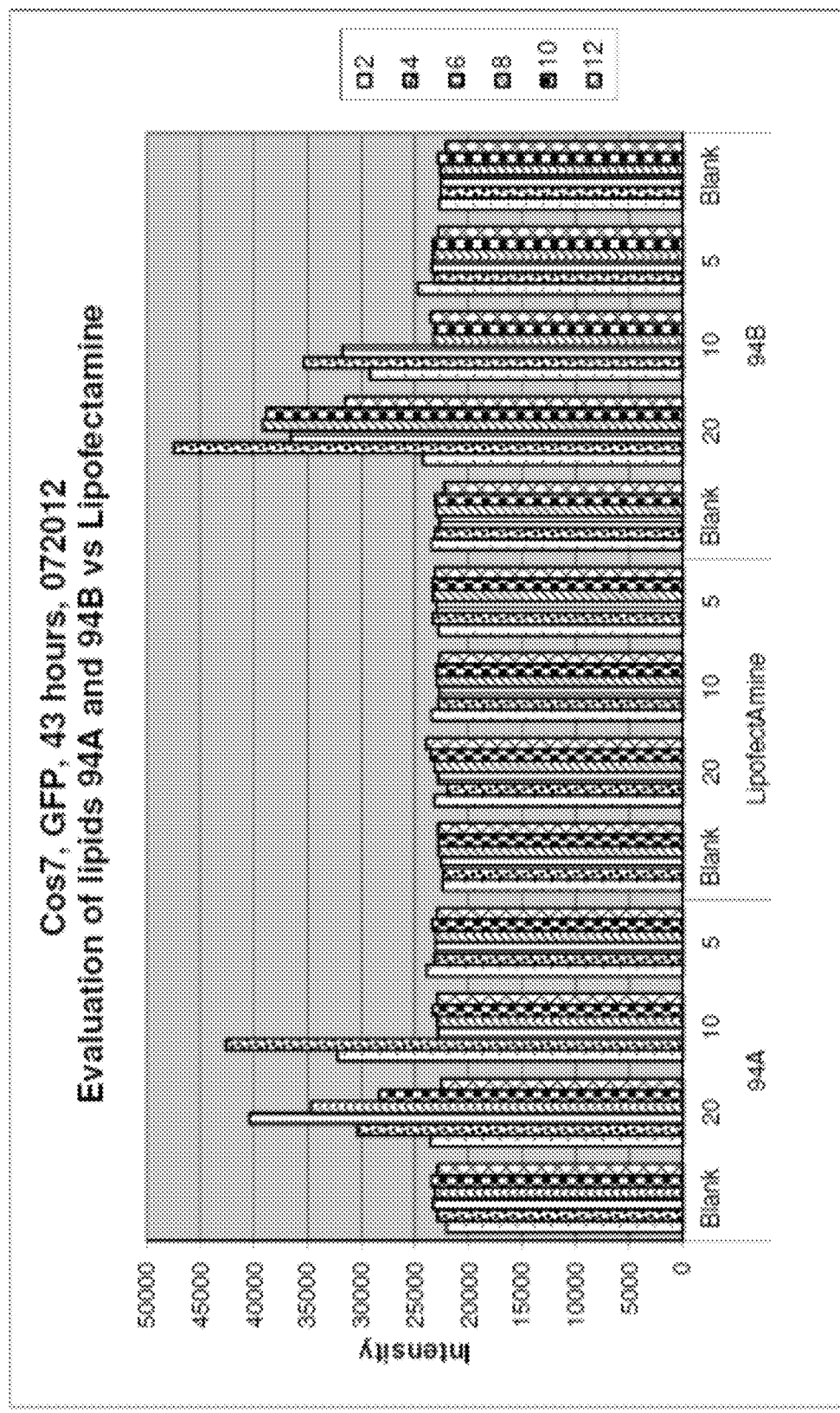
FIG. 4 shows the transfection evaluation of lipids 94-a and 94-b in Cos-7 cells. The delivery and expression of the plasmid CMV•GFP in Cos-7 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 5:
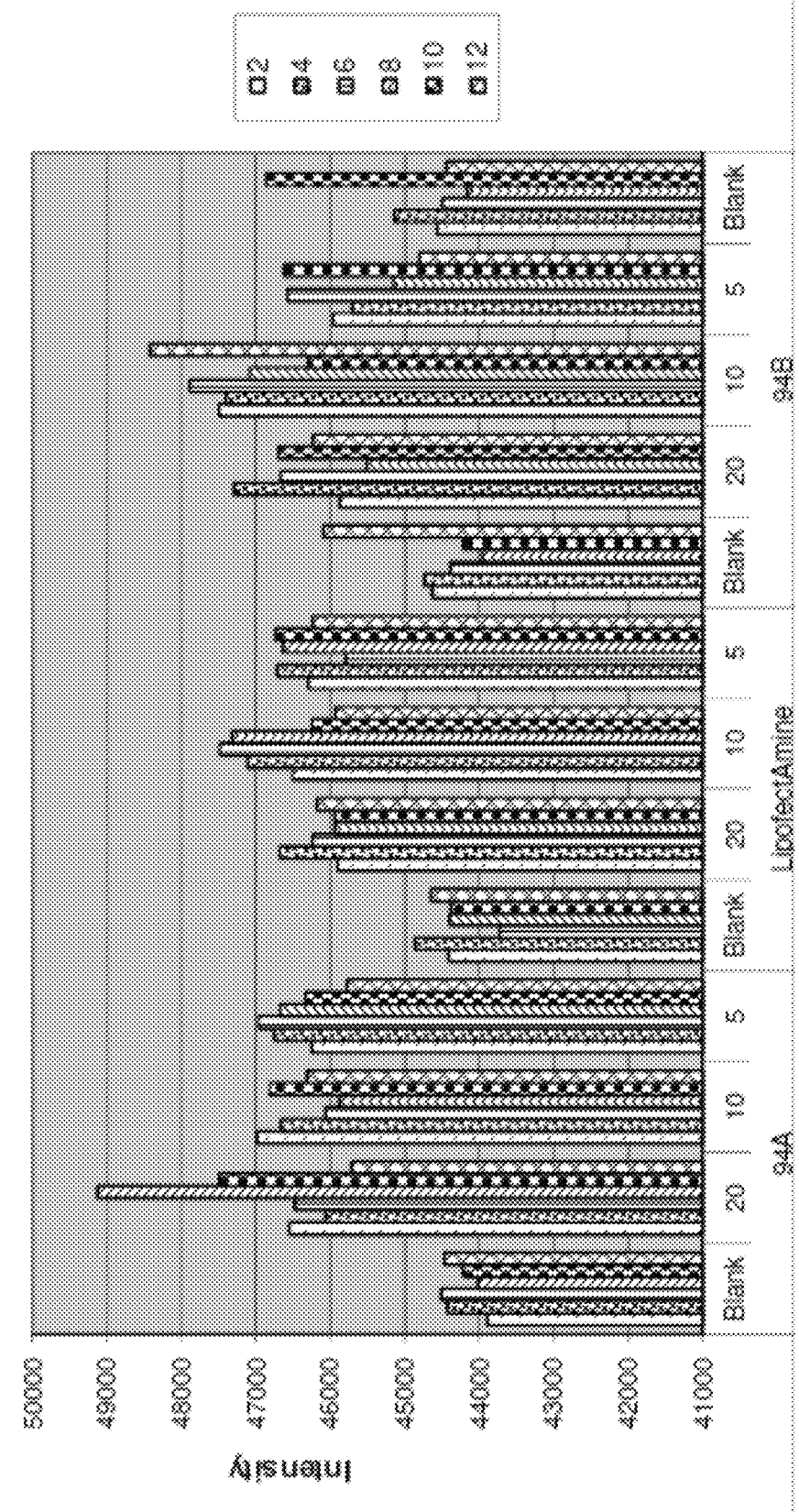
FIG. 5 shows the transfection evaluation of lipids 94-a and 94-b in HDFa cells. The delivery and expression of the plasmid CMV•GFP in HDFa cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 6:
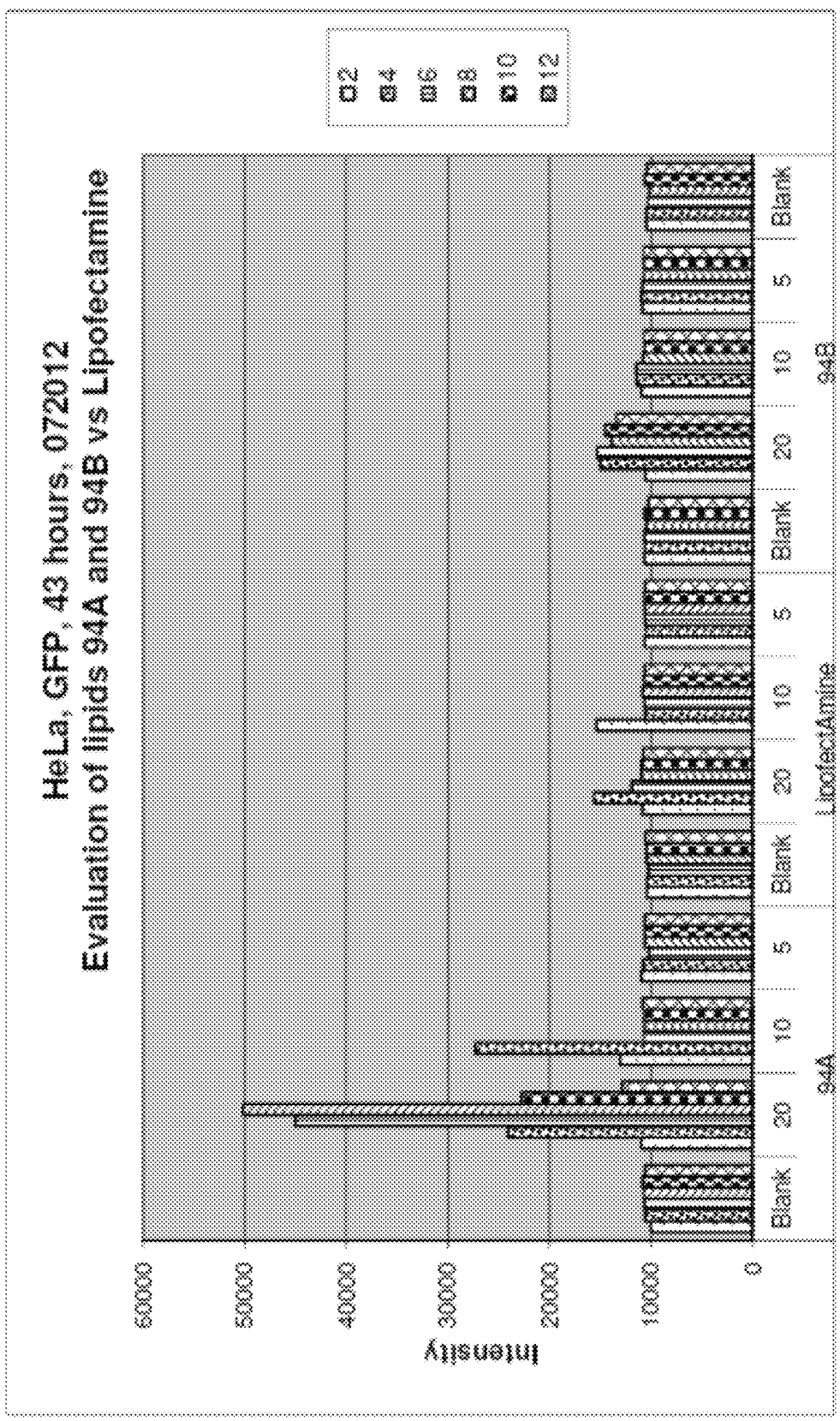
FIG. 6 shows the transfection evaluation of lipids 94-a and 94-b in HeLa cells. The delivery and expression of the plasmid CMV•GFP in HeLa cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 7:
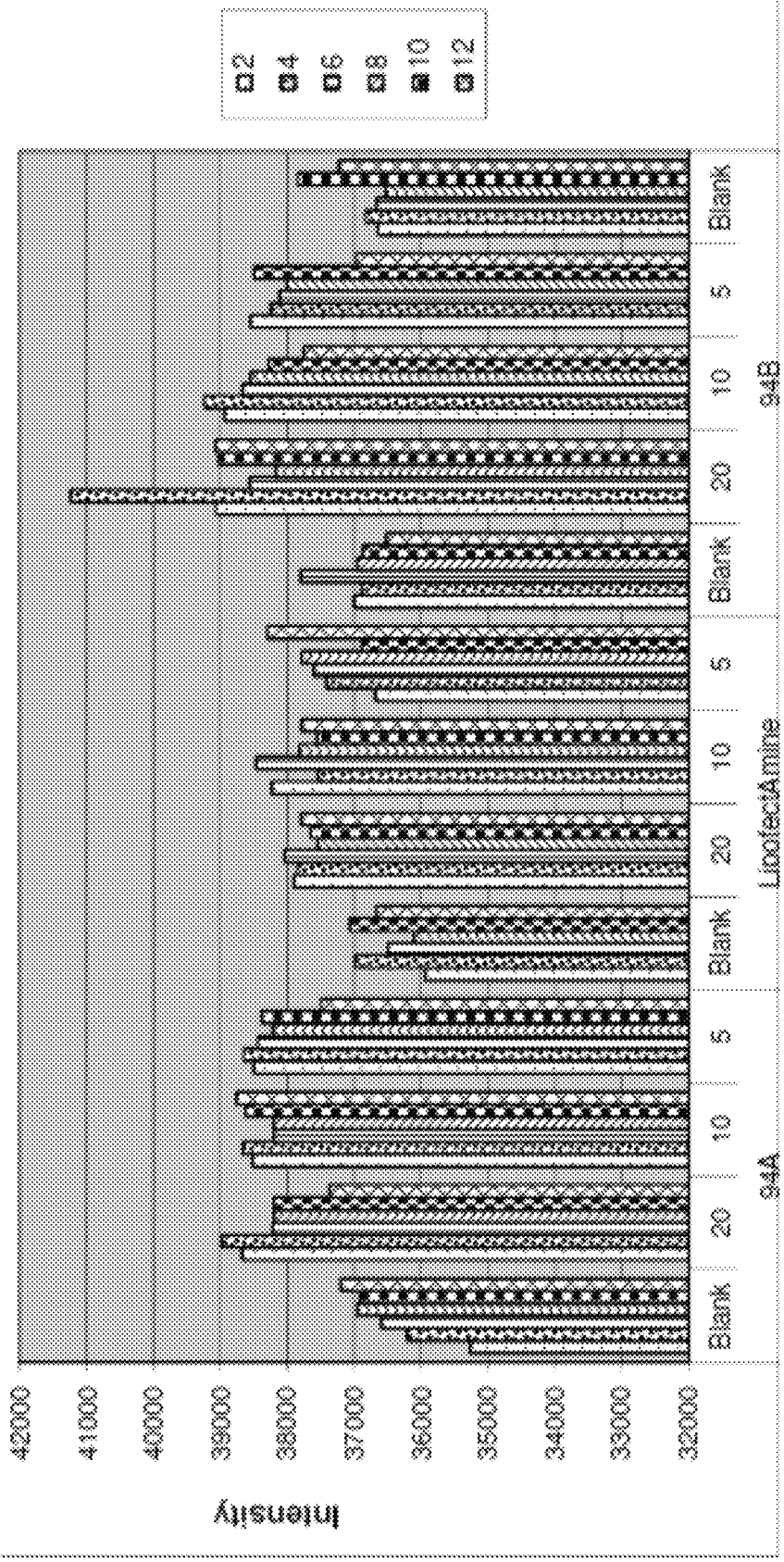
FIG. 7 shows the transfection evaluation of lipids 94-a and 94-b in HepG2 cells. The delivery and expression of the plasmid CMV•GFP in HepG2 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 8:
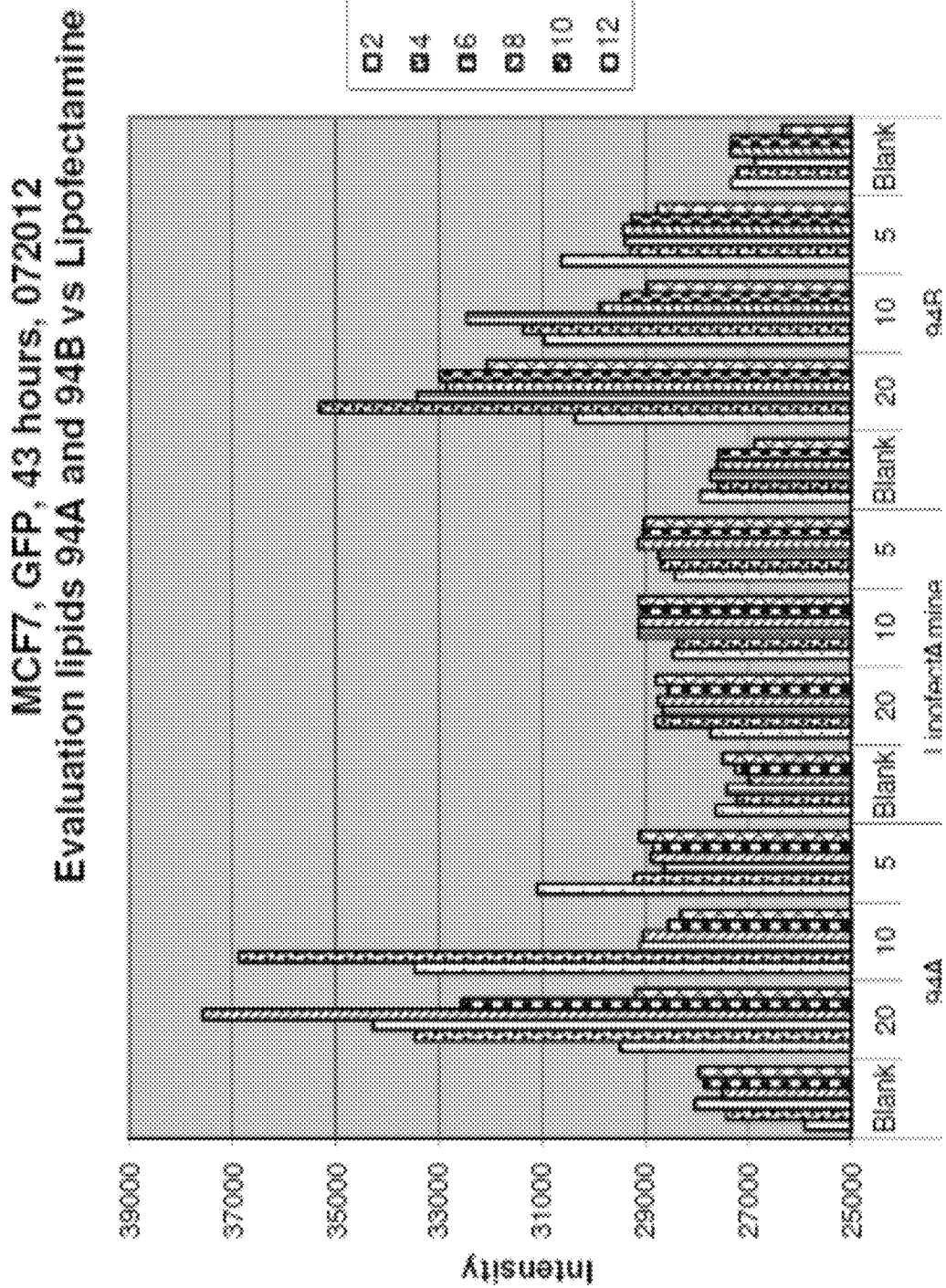
FIG. 8 shows the transfection evaluation of lipids 94-a and 94-b in MCF-7 cells. The delivery and expression of the plasmid CMV•GFP in MCF-7 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time
Figure 9:
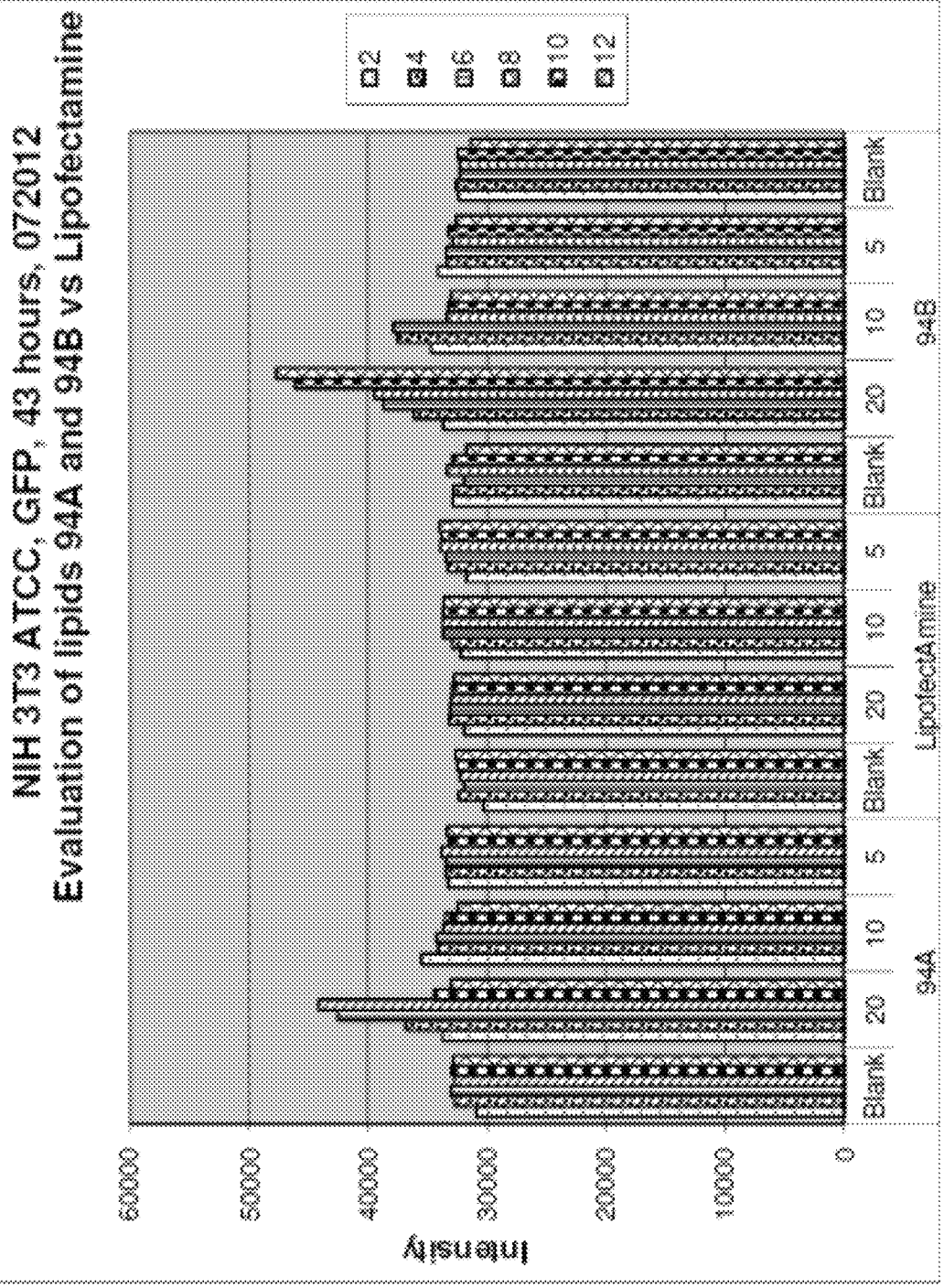
FIG. 9 shows the transfection evaluation of lipids 94-a and 94-b in NIH 3T3 cells. The delivery and expression of the plasmid CMV•GFP in NIH 3T3 cells using 94-a or 94-b was compared with LipofectAmine. Different amounts of the transfection reagents (2, 4, 6, 8, 10, 12 μl) are complexed with different concentrations of DNA (5, 10, 20 μg/ml) and 10 μl of the complex is applied to the cells. Florescence is measured after incubating for the indicated time.

The lipids formulated in this manner were used in transfection. The transfection of 293, CHO-K1, NIH3T3, Hela, A549, MCF-7, HepG2, HDF-a, and Cos-7 with green fluorescent protein reporter plasmid pCMV•GFP was carried out using the formulations 94-a and 94-b, which contain the spermine analog Compound 4A. These results are shown in FIGS. 1-9.

Reagent Kits

Components of the transfection compositions described above can be provided in a reagent kit. The kits contain the lipid of Formula I, together with additional components, such as a neutral lipid, a cationic lipid, cell surface ligands, fusion agents, amphipathic peptide and/or nuclear localization agents and the like. The kit components may be separate or may be premixed in any manner. For example, the lipid of Formula I may be admixed with one or more neutral lipid. Additional components may also be present in the same container or may be present in one or more separate containers. The kits typically include vessels, such as vials and/or tubes, which are packaged together, for example in a cardboard box. The kits can be shipped from a supplier to a customer. For example, in one example provided herein is a kit that includes a vial that includes a liposomal formulation as described above and, optionally, a transfection agent and a transfection enhancing peptide. The kit can also include, for example, a separate vessel that includes a transfection enhancing agent, such as a transfection enhancing peptide, for example Plus Reagent™ (Invitrogen Corp., Carlsbad, CA). The kit can also include in separate containers, cells, cell culture medium, and a reporter nucleic acid sequence, such as a plasmid that expresses a reporter gene. In certain examples, the culture medium can be reduced-serum medium and/or protein expression medium.

In one embodiment, a kit comprises individual portions of, or a mixture of, cationic lipid, such as a lipid of Formula I, and peptide, protein or fragment thereof or modified peptide, protein or fragment thereof. In another embodiment, a kit comprises individual portions of, or a mixture of, polycationic polymers and peptide, protein or fragments thereof or modified peptide, protein or fragments thereof. Cationic lipid transfection kits can optionally include neutral lipid as well as other transfection-enhancing agents or other additives, and the relative amounts of components in the kit may be adjusted to facilitate preparation of transfection compositions. Kit components can include appropriate medium or solvents for other kit components.

Nucleic acids that can be transfected by the methods of this invention include DNA and RNA (including RNAi/siRNA) of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays (e.g., diagnostic nucleic acids). Therapeutic nucleic acids include those nucleic acids that encode or can express therapeutically useful proteins, peptides or polypeptides in cells, those which inhibit undesired expression of nucleic acids in cells, and those which inhibit undesired enzymatic activity or activate desired enzymes in cells. The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

The present invention, thus generally described, will be understood more readily by reference to the following examples, which are provided by way of illustration and are not intended to be limiting of the present invention.

The following examples are provided in order to demonstrate and further illustrate certain preferred embodiments and aspects of the present invention and are not to be construed as limiting the scope thereof.

EXAMPLES

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Example 1: Synthesis of 1,2-Dipalmitoleoyl-sn-glycero-3-O-methyl-phosphoethanol-amine-N-carboxylspermine (Compound 4b in Scheme I)

BOC protected 5-carboxyspermine (1.342 g, 2 mmole) was treated with N,N'-diisopropylcarbodiimide (DIPCDI) (0.358 g, 2 mmole) and N-hydroxysuccinimide (0.236 g, 2 mmole) in 10 ml of DMF/CH$_2$Cl$_2$ (1:1) for 2 hrs. 1,2-Dipalmitoleyl-sn-glycero-3-phosphoethanoleamine (DPPE) (1.0 g, 1.45 mmole and diisopropylethylamine (0.56 ml, 2 mmole) were dissolved in 5 ml of DMF/CH$_2$Cl$_2$ and added to the activated acid. The reaction mixture was stirred overnight at room temperature and diluted with 200 ml chloroform and extracted one time with water. The organic phase was separated and volume reduced to ~10 ml on the rotary evaporator and loaded on a silica flash column equilibrated with chloroform. The column was eluted using a methanol/chloroform gradient (0-20%). The fractions containing the desired material were combined and solvent removed on the rotary evaporator to obtain a gum of compound 2 (R=C$_{16}$H$_{31}$, M+ 1316.5). The gum was dissolved in 10 ml ethyl ether and treated with 0.5 ml of methyl triflate. The reaction mixture was stirred overnight and diluted with 200 ml chloroform and extracted with 200 ml water. The organic layer was separated and concentrated to a gum. The gum was dissolved in 10 ml CH$_2$Cl$_2$ and treated with 5 ml trifluroacetic acid. The mixture was stirred at room temperature for 1 hr and concentrated on the rotary evaporator. The desired 1,2-dipalmitoleoyl-sn-glycero-3-O-methylphosphoethanolamine-N-carboxylspermine (4b) was obtained after subjecting the residue to flash chromatography (C18-silica, step gradient 60/40 methanol/water, 70/30 methanol/water, 80/20 methanol/water to 100% methanol). It was characterized by ESMS (M+ 930.6).

The dioleyl (4a), dipalmitoyl (4c) and dimyristoyl (4d) analogs were synthesized in a similar manner (Compounds 4a, 4c, and 4d in Scheme I).

In a similar fashion, compounds 7a-7d in Scheme II, were synthesized starting from 1,2-dioleoyl-sn-glycero-3-phosphoethanolamine (DOPE) and the corresponding BOC protected amino acid.

Example 2: Formulation of Cationic Lipids into Liposomes

The liposome was formulated using reverse evaporation. Thus, 15.89 mg of the trifluoroacetic acid (TFA) salt of Compound 4a (R=oleyl) and 4.10 mg of DOPE (2:1 molar ratio of TFA salt of Compound 4a:DOPE) were combined and placed in a round bottom flask. The lipid mixture was dissolved in 2 ml of chloroform. 10 ml of water was added to the chloroform solution. The chloroform was removed under vacuum on a rotary evaporator to obtain a liposome solution. The solution was adjusted to 10 ml to obtain a 2 mg/ml liposome solution. This liposomal solution is designated as lipid "94-a". In addition, a 1:1 liposomal formulation designated as lipid "94-b" was prepared as above by using 13.19 mg of Compound 4a and 6.81 mg of DOPE. Similar liposomal formulations where the molar ratios varied from 2:1 to 1:16 (TFA salt of Compound 4a:DOPE) were prepared in this manner. Compounds 4b, 4c and 4d were also formulated in the same manner to provide additional liposomal formulations.

Example 3: Transfection Protocol for Liposomal Formulations 94-a and 94-b

Transfection of 8 different cell types with green florescent protein reporter plasmid pCMV•GFP was carried out as follows:

Cells were plated in 96-well plates with 100 µl of media containing 5-10% fetal calf serum the day prior to transfection such that a desired confluency (70%-95%) was achieved. The following day a transfection agent that included a liposomal composition of the lipids 94-a (2 mg/ml) and 94-b (2 mg/ml) and DNA were mixed in Opti-MEM to form DNA/lipid complexes. Complexes were formed by adding various amounts of lipids in Opti-MEM (2 µl to 12 µl lipid to 50 µl of Opti-MEM) to 50 µl Opti-MEM DNA solution. DNA solutions were at 10, 20, 40 ug/ml. The DNA and lipid solutions were then mixed to form DNA lipid complexes. The complexes were incubated for at least 20 minutes after which 10 µl DNA/lipid complexes were added to cells. LipofectAmine™ (Invitrogen, Carlsbad, CA) were used as described by the manufacturer.

Cells were incubated for an additional 24 hours to 48 hrs to allow expression of the plasmid. Total fluorescence's of each well was read on a fluorescence plate reader. The results are given in FIGS. 1-9.

Although the disclosure has been described with reference to the above examples, it will be understood that modifications and variations are encompassed within the spirit and scope of the disclosure. Accordingly, the disclosure is limited only by the following claims.

---

What is claimed is:

1. A compound of Formula I:

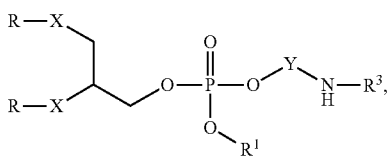

or a pharmaceutically acceptable salt thereof, wherein:
  each X independently is selected from —C(O)O— and —O(O)C;
  Y is selected from methyl, ethyl, n-propyl, isopropyl, n-butyl, isobutyl, sec-butyl, tert-butyl, pentyl, isoamyl, and n-hexyl;
  each R is independently selected from $(C_2-C_{20})$alkyl and $(C_2-C_{20})$alkenyl;
  $R^1$ is independently selected from —$CH_3$, —$CH_2CH_3$, —$CH_2CH_2CH_3$, and —$CH_2CH_2CH_2CH_3$; and
  $R^3$ is independently selected from —$CH_2NH_2$, —C(O)CH($NH_2$)($CH_2$)$_3NH_2$, —C(O)CH($NH_2$)($CH_2$)$_3$NHC(=NH)$NH_2$, —C(O)CH($NH_2$)($CH_2$)($C_3H_3N_2$), —C(O)CH($NH_2$)$CH_2NH_2$, and —C(O)CH($NH_2$)($CH_2$)$_2NH_2$.

2. The compound of claim 1, wherein:
  Y is selected from methyl, ethyl, n-propyl, isopropyl, n-butyl, isobutyl, sec-butyl, and tert-butyl;
  each R is independently selected from $(C_2-C_{20})$alkenyl.

3. The compound of claim 2, wherein:
  Y is selected from methyl, ethyl, n-propyl, or isopropyl.

4. The compound of claim 3, wherein:
  Y is $CH_2CH_2$.

5. A composition comprising a compound of Formula of claim 1 and at least one or more neutral lipids.

6. A composition comprising a compound of Formula I of claim 1, and at least one or more cationic lipids, and/or at least one or more neutral lipids.

7. A composition comprising a compound of Formula I of claim 1, and one or more polyamine transfection agents.

8. A composition comprising a compound of Formula I of claim 1, and one or more fusion agents.

9. A composition comprising a compound of Formula I of claim 1, and one or more cell surface ligands, wherein said one or more cell surface ligands optionally comprises a polycationic nucleic acid binding moiety.

10. A composition comprising a compound of Formula I of claim 1, and one or more nuclear localization peptides or one or more protein cell surface ligands, wherein said one or more nuclear localization peptides or said one or more protein cell surface ligands optionally comprises a polycationic nucleic acid binding moiety.

11. A composition comprising a compound of Formula I of claim 1, and one or more amphipathic peptides, wherein said one or more amphipathic peptide optionally is covalently linked to a polycationic nucleic binding moiety, and wherein said amphipathic peptide optionally functions as a fusion agent.

12. A composition comprising a compound of Formula I of claim 1, further comprising one or more nucleic acids.

13. The composition of claim 12, wherein the one or more nucleic acids are selected from DNA and RNA.

14. The composition of claim 13, wherein the RNA is an RNAi molecule.

15. A method of introducing a nucleic acid, protein, or peptide into a eukaryotic cell, comprising contacting the cell with the nucleic acid, protein, or peptide and a composition according to claim 12.

16. The method of claim 15, wherein the cell is a human cell.

17. The method of claim 15, wherein the cell is an animal cell.

18. A method of expressing a protein in a cell, comprising contacting the cell with an expression vector encoding the protein and a compound of Formula I of claim 1.

19. A method of inhibiting expression of a protein in a cell, comprising contacting the cell with an RNAi molecule and a compound of Formula I of claim 1.

20. The composition of claim 1, further comprising a polycationic nucleic acid binding moiety.

21. The composition of claim 20, wherein the polycationic nucleic acid binding moiety is selected from the group consisting of PEI, spermine, spermidine, carboxyspermine and combinations thereof.

22. The composition of claim 20, wherein the polycationic nucleic acid binding moiety comprises a polybasic peptide, wherein said polybasic peptide is selected from the group consisting of poly-lysine, poly-ornithine, poly-histidine, poly-arginine, and combinations thereof.

* * * * *

SEQUENCE LISTING

```
<160> NUMBER OF SEQ ID NOS: 31

<210> SEQ ID NO 1
<211> LENGTH: 15
<212> TYPE: PRT
<213> ORGANISM: Artificial Sequence
<220> FEATURE:
<223> OTHER INFORMATION: Artificial peptide

<400> SEQUENCE: 1

Gly Tyr Ser Thr Pro Pro Lys Lys Lys Arg Lys Val Glu Asp Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Artificial peptide

<400> SEQUENCE: 2

Gly Tyr Ser Thr Pro Pro Lys Thr Arg Arg Arg Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Artificial peptide

<400> SEQUENCE: 3

Gly Tyr Ser Thr Pro Gly Arg Lys Lys Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Artificial peptide
```

-continued

```
<400> SEQUENCE: 4

Gly Tyr Ser Thr Pro Arg Arg Asn Arg Arg Arg Trp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Artificial peptide

<400> SEQUENCE: 5

Pro Asp Glu Val Lys Arg Lys Lys Lys Pro Pro Thr Ser Tyr Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Artificial peptide

<400> SEQUENCE: 6

Pro Arg Arg Arg Thr Lys Pro Pro Thr Ser Tyr Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Artificial peptide

<400> SEQUENCE: 7

Arg Lys Lys Arg Gly Pro Thr Ser Tyr Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Artificial peptide

<400> SEQUENCE: 8

Trp Arg Arg Arg Arg Asn Arg Arg Pro Thr Ser Tyr Gly
1               5                   10

<210> SEQ ID NO 9
<211> LENGTH: 58
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (18)..(58)
<223> OTHER INFORMATION: 0-32 of the lysine residues may be absent

<400> SEQUENCE: 9

Gly Tyr Gly Pro Pro Lys Lys Arg Lys Val Glu Ala Pro Tyr Lys
1               5                   10                  15

Ala Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys Lys
```

```
                35                  40                  45
Lys Lys Lys Lys Lys Lys Lys Lys Lys
    50                  55

<210> SEQ ID NO 10
<211> LENGTH: 14
<212> TYPE: PRT
<213> ORGANISM: Artificial Sequence
<220> FEATURE:
<223> OTHER INFORMATION: Artificial peptide

<400> SEQUENCE: 10

Phe Glu Ala Ala Leu Ala Glu Ala Leu Ala Glu Ala Leu Ala
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Artificial peptide

<400> SEQUENCE: 11

Leu Ala Arg Leu Leu Pro Arg Leu Leu Ala Arg Leu
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Artificial peptide

<400> SEQUENCE: 12

Gly Leu Leu Glu Glu Leu Leu Glu Leu Leu Glu Glu Leu Trp Glu Glu
1               5                   10                  15

Leu Leu Glu Gly
            20

<210> SEQ ID NO 13
<211> LENGTH: 19
<212> TYPE: PRT
<213> ORGANISM: Artificial Sequence
<220> FEATURE:
<223> OTHER INFORMATION: Artificial peptide

<400> SEQUENCE: 13

Gly Trp Glu Gly Leu Ile Glu Gly Ile Glu Gly Gly Trp Glu Gly Leu
1               5                   10                  15

Ile Glu Gly

<210> SEQ ID NO 14
<211> LENGTH: 20
<212> TYPE: PRT
<213> ORGANISM: Artificial Sequence
<220> FEATURE:
<223> OTHER INFORMATION: Artificial peptide

<400> SEQUENCE: 14

Gly Leu Phe Glu Ala Leu Ala Glu Phe Ile Glu Gly Gly Trp Glu Gly
1               5                   10                  15

Leu Ile Glu Gly
            20
```

```
<210> SEQ ID NO 15
<211> LENGTH: 20
<212> TYPE: PRT
<213> ORGANISM: Artificial Sequence
<220> FEATURE:
<223> OTHER INFORMATION: Artificial peptide

<400> SEQUENCE: 15

Gly Leu Phe Glu Ala Leu Leu Glu Leu Leu Glu Ser Leu Trp Glu Leu
1               5                   10                  15

Leu Leu Glu Ala
            20

<210> SEQ ID NO 16
<211> LENGTH: 22
<212> TYPE: PRT
<213> ORGANISM: Artificial Sequence
<220> FEATURE:
<223> OTHER INFORMATION: Artificial peptide

<400> SEQUENCE: 16

Gly Gly Tyr Cys Leu Glu Lys Trp Met Ile Val Ala Ser Glu Leu Lys
1               5                   10                  15

Cys Phe Gly Asn Thr Ala
            20

<210> SEQ ID NO 17
<211> LENGTH: 23
<212> TYPE: PRT
<213> ORGANISM: Artificial Sequence
<220> FEATURE:
<223> OTHER INFORMATION: Artificial peptide

<400> SEQUENCE: 17

Gly Gly Tyr Cys Leu Thr Arg Trp Met Leu Ile Glu Ala Glu Leu Lys
1               5                   10                  15

Cys Phe Gly Asn Thr Ala Val
            20

<210> SEQ ID NO 18
<211> LENGTH: 30
<212> TYPE: PRT
<213> ORGANISM: Artificial Sequence
<220> FEATURE:
<223> OTHER INFORMATION: Artificial peptide

<400> SEQUENCE: 18

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 19
<211> LENGTH: 15
<212> TYPE: PRT
<213> ORGANISM: Artificial Sequence
<220> FEATURE:
<223> OTHER INFORMATION: Artificial peptide

<400> SEQUENCE: 19

Ile Asn Ile Gly Thr Thr Gly Trp Gly Asp His Tyr Ser Leu Tyr
1               5                   10                  15

<210> SEQ ID NO 20
<211> LENGTH: 21
```

```
<212> TYPE: PRT
<213> ORGANISM: Artificial Sequence
<220> FEATURE:
<223> OTHER INFORMATION: Artificial peptide

<400> SEQUENCE: 20

Ala Ala Arg Ser Pro Ser Tyr Tyr Arg Tyr Asp Tyr Gly Pro Tyr Tyr
1               5                   10                  15
Ala Met Asp Tyr Asp
            20

<210> SEQ ID NO 21
<211> LENGTH: 12
<212> TYPE: PRT
<213> ORGANISM: Artificial Sequence
<220> FEATURE:
<223> OTHER INFORMATION: Artificial peptide

<400> SEQUENCE: 21

Gly Ala Cys Ser Glu Arg Ser Met Asn Phe Cys Gly
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Artificial peptide

<400> SEQUENCE: 22

Gly Ala Cys Tyr Gly Leu Pro His Lys Phe Cys Gly
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Artificial peptide

<400> SEQUENCE: 23

Tyr Tyr Cys Gln Gln Arg Ser Ser Tyr Pro Tyr Thr Phe Gly Gly
1               5                   10                  15

<210> SEQ ID NO 24
<211> LENGTH: 22
<212> TYPE: PRT
<213> ORGANISM: Artificial Sequence
<220> FEATURE:
<223> OTHER INFORMATION: Artificial peptide

<400> SEQUENCE: 24

Thr Arg Gln Ala Arg Arg Asn Arg Arg Arg Arg Trp Arg Glu Arg Gln
1               5                   10                  15
Arg Gly Ser Gly Ser Gly
            20

<210> SEQ ID NO 25
<211> LENGTH: 18
<212> TYPE: PRT
<213> ORGANISM: Artificial Sequence
<220> FEATURE:
<223> OTHER INFORMATION: Artificial peptide

<400> SEQUENCE: 25

Arg Asp Trp Ser Ser Gln His Pro Gly Arg Cys Asn Gly Glu Thr His
```

Leu Lys

<210> SEQ ID NO 26
<211> LENGTH: 20
<212> TYPE: PRT
<213> ORGANISM: Artificial Sequence
<220> FEATURE:
<223> OTHER INFORMATION: Artificial peptide

<400> SEQUENCE: 26

Gly Gly Gly Asp Tyr Tyr Cys Ala Ala Trp Asp Asp Ser Leu Asn Gly
1               5                   10                  15

Tyr Ser Val Phe
            20

<210> SEQ ID NO 27
<211> LENGTH: 24
<212> TYPE: PRT
<213> ORGANISM: Artificial Sequence
<220> FEATURE:
<223> OTHER INFORMATION: Artificial peptide

<400> SEQUENCE: 27

Val Ile Val Thr Gly Gly Asp Tyr Ser Phe Ala Leu Pro Val Gly Gln
1               5                   10                  15

Trp Pro Val Met Thr Gly Gly Ala
            20

<210> SEQ ID NO 28
<211> LENGTH: 23
<212> TYPE: PRT
<213> ORGANISM: Artificial Sequence
<220> FEATURE:
<223> OTHER INFORMATION: Artificial peptide

<400> SEQUENCE: 28

Asp Lys Pro Ser Tyr Gln Phe Gly Gly His Asn Ser Val Asp Phe Glu
1               5                   10                  15

Glu Asp Thr Leu Pro Lys Val
            20

<210> SEQ ID NO 29
<211> LENGTH: 15
<212> TYPE: PRT
<213> ORGANISM: Artificial Sequence
<220> FEATURE:
<223> OTHER INFORMATION: Artificial peptide

<400> SEQUENCE: 29

His Leu Arg Arg Leu Arg Arg Arg Leu Leu Arg Glu Ala Glu Gly
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Artificial peptide

<400> SEQUENCE: 30

Tyr Tyr Cys Ala Arg Ser Gly Tyr Tyr Ala Met Asp Tyr Trp Gly Gln
1               5                   10                  15

Gly Thr

```
<210> SEQ ID NO 31
<211> LENGTH: 12
<212> TYPE: PRT
<213> ORGANISM: Artificial Sequence
<220> FEATURE:
<223> OTHER INFORMATION: Artificial peptide

<400> SEQUENCE: 31

Gly Lys Trp Glu Arg Lys Pro Ile Arg Cys Ala Ser
1               5                   10
```